United States Patent
Tripp et al.

(10) Patent No.: US 6,455,039 B2
(45) Date of Patent: Sep. 24, 2002

(54) ANTI-PARASITIC HELMINTH MACROPHAGE MIGRATION INHIBITORY FACTOR ANTIBODIES AND USES THEREOF

(75) Inventors: Cynthia Ann Tripp, Ft. Collins; Kevin S. Brandt, Windsor; Nancy Wisnewski, Ft. Collins, all of CO (US)

(73) Assignee: Heska Corporation, Ft. Collins, CO (US)

( * ) Notice: Subject to any disclaimer, the term of this patent is extended or adjusted under 35 U.S.C. 154(b) by 0 days.

(21) Appl. No.: 09/774,377

(22) Filed: Jan. 30, 2001

Related U.S. Application Data

(62) Division of application No. 08/906,480, filed on Aug. 5, 1997, now Pat. No. 6,207,158, which is a division of application No. 08/558,735, filed on Nov. 16, 1995, now Pat. No. 5,681,724.

(51) Int. Cl.$^7$ .............. C12Q 1/68; C12P 7/56; C12P 7/28; C07K 16/00
(52) U.S. Cl. .............. 424/130.1; 424/139.1; 424/150.1; 530/387.1; 530/388.1; 530/387.9
(58) Field of Search ............ 424/130.1, 139.1, 424/150.1; 530/387.1, 387.9, 388.1

(56) References Cited

U.S. PATENT DOCUMENTS

| | | |
|---|---|---|
| 5,021,342 A | 6/1991 | Greene et al. |
| 5,328,990 A | 7/1994 | Wistow |
| 5,416,009 A | 5/1995 | Lazzeri et al. |
| 5,569,603 A | 10/1996 | Tripp et al. |

OTHER PUBLICATIONS

Bernhagen et al., 1993, *Nature*, 365:756–759.
Blocki et al., 1992, *Nature*, 360:269–270.
Blocki et al., 1993, *Protein Sci.*, 2:2095–2102.
Brophy et al., 1995, *J. Parasitol.*, 81(2):302–303.
Calandra et al., 1995, *Nature*, 377:68–71.
David, 1993, *Parasitol. Today*, 9(9):315–316.
Diaz–Guerra et al., 1992, *Arch. Med. Res.*, 23(2):151–152.
Galat et al., 1993, *FEBS*, 319(3):233–236.
Kretschmer et al., 1991, *Parasitol. Res.*, 77:374–378.
Lanzer et al., *Nucleic Acids Research*, 20(12) 3051–3056 (1992).
Oppenheim et al., 1994, *FASEB J.*, 8:158–162.
Rico et al., 1995, *Parasitol. Res.*, 81:158–162.
Sakai et al., 1994, *Biochem. Mol. Biol. Int'l.*, 33(3):439–446.
Weiser et al., 1989, *Proc. Natl. Acad. Sci. USA*, 86:7522–7526.
Wistow et al., 1993, *Proc. Natl. Acad. Sci. USA*, 90:1272–1275.

*Primary Examiner*—Mark Navarro
*Assistant Examiner*—Iesha Fields
(74) *Attorney, Agent, or Firm*—Sheridan Ross P.C.

(57) ABSTRACT

The present invention relates to parasitic helminth macrophage migration inhibitory factor (MIF) proteins; to parasitic helminth MIF nucleic acid molecules, including those that encode such MIF proteins; to antibodies raised against such MIF proteins; and to compounds that inhibit parasitic helminth MIF activity. The present invention also includes methods to obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to protect animals from diseases caused by parasitic helminths.

9 Claims, No Drawings

ANTI-PARASITIC HELMINTH MACROPHAGE MIGRATION INHIBITORY FACTOR ANTIBODIES AND USES THEREOF

This application is a divisional of U.S. patent application Ser. No. 08/906,480, filed Aug. 5, 1997, entitled "Parasitic Helminth Macrophage Migration Inhibitory Factor Proteins and Uses Thereof", now U.S. Pat. No. 6,207,158, which is a divisional of U.S. patent application Ser. No. 08/558,735, filed Nov. 16, 1995, entitled "Parasitic Helminth Macrophage Migration Inhibitory Factor Nucleic Acid Molecules and Uses Thereof", now U.S. Pat. No. 5,681,724, issued Oct. 28, 1997.

FIELD OF THE INVENTION

The present invention relates to parasitic helminth macrophage migration inhibitory factor (MIF) nucleic acid molecules, proteins encoded by such nucleic acid molecules, antibodies raised against such proteins, and inhibitors of such proteins. The present invention also includes therapeutic compositions comprising such nucleic acid molecules, proteins, antibodies, and/or inhibitors, as well as their use to protect animals from diseases caused by parasitic helminths, such as heartworm or onchocerciasis.

BACKGROUND OF THE INVENTION

Parasitic helminth infections in animals, including humans, are typically treated by chemical drugs, because there are essentially no efficacious vaccines available. One disadvantage with chemical drugs is that they must be administered often. For example, dogs susceptible to heartworm are typically treated monthly to maintain protective drug levels. Repeated administration of drugs to treat parasitic helminth infections, however, often leads to the development of resistant helminth strains that no longer respond to treatment. Furthermore, many of the chemical drugs cause harmful side effects in the animals being treated, and as larger doses become required due to the build up of resistance, the side effects become even greater. Moreover, a number of drugs only treat symptoms of a parasitic disease but are unable to prevent infection by the parasitic helminth.

It is particularly difficult to develop vaccines against parasitic helminth infections both because of the complexity of the parasite's life cycle and because, while administration of parasites or parasite antigens can lead to the production of a significant antibody response, the immune response is typically not sufficient to protect the animal against infection.

As an example of the complexity of parasitic helminths, the life cycle of *D. immitis*, the helminth that causes heartworm, includes a variety of life forms, each of which presents different targets, and challenges, for immunization. Adult forms of the parasite are quite large and preferentially inhabit the heart and pulmonary arteries of an animal. Sexually mature adults, after mating, produce microfilariae which traverse capillary beds and circulate in the vascular system of the dog. One method of demonstrating infection in the dog is to detect the circulating microfilariae.

If the dog is maintained in an insect-free environment, the life cycle of the parasite cannot progress. However, when microfilariae are ingested by the female mosquito during blood feeding on an infected dog, subsequent development of the microfilariae into larvae occurs in the mosquito. The microfilariae go through two larval stages (L1 and L2) and finally become mature third stage larvae (L3) which can then be transmitted back to the dog through the bite of the mosquito. It is this L3 stage, therefore, that accounts for the initial infection. As early as three days after infection, the L3 molt to the fourth larval (L4) stage, and subsequently to the fifth stage, or immature adults. The immature adults migrate to the heart and pulmonary arteries, where they mature and reproduce, thus producing the microfilariae in the blood. "Occult" infection with heartworm in dogs is defined as that wherein no microfilariae can be detected, but the existence of the adult heartworms can be determined through thoracic examination.

Heartworm not only is a major problem in dogs, which typically cannot even develop immunity upon infection (i.e., dogs can become reinfected even after being cured by chemotherapy), but is also becoming increasingly widespread in other companion animals, such as cats and ferrets. Heartworm infections have also been reported in humans. Other parasitic helminthic infections are also widespread, and all require better treatment, including a preventative vaccine program. *O. volvulus*, for example, causes onchocerciasis (also known as river blindness) in humans. Up to 50 million people throughout the world are reported to be infected with *O. volvulus*, with over a million being blinded due to infection.

Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic helminths. Although a number of prominent antigens have been identified in several parasitic helminths, including in Dirofilaria and Onchocerca, there is yet to be an effective vaccine developed for any parasitic helminth.

As such, there remains a need to identify an efficacious composition that protects animals against diseases caused by parasitic helminths and that, preferably, also protects animals from infection by such helminths.

Macrophage migration inhibitory factors (MIFs), which are about 13 kilodaltons (kD) in size, have been identified in several mammalian and avian species; see, for example, Galat et al, 1993, *Fed. Eur. Biochem. Soc.* 319, 233–236, Wistow et al, 1993, *Proc. Natl. Acad. Sci. USA* 90, 1272–1275, Weiser et al, 1989, *Proc. Natl. Acad. Sci. USA* 86, 7522–7526, Bernhagen, et al, 1993, *Nature* 365, 756–759, Blocki et al, 1993, *Protein Science* 2, 2095–2102, and Blocki et al, 1992, *Nature* 360, 269–270. Although MIF was first characterized as being able to block macrophage migration, MIF also appears to effect macrophage-macrophage adherence; induce macrophage to express interleukin-1-beta, interleukin-6, and tumor necrosis factor alpha; up-regulate HLA-DR; increase nitric oxide synthase and nitric oxide concentrations; and activate macrophage to kill *Leishmania donovani* tumor cells and inhibit *Mycoplasma avium* growth, by a mechanism different from that effected by interferon-gamma. In addition to its potential role as an immunoevasive molecule, MIF can act as an immunoadjuvant when given with bovine serum albumin or HIV gp120 in incomplete Freunds or liposomes, eliciting antigen induced proliferation comparable to that of complete Freunds.

MIF appears to be related to glutathione S-transferase (GST) since at least some MIFs have GST activity and are able to bind to glutathione. MIFs, however, are only about half the size of GST subunits and do not show activity against 1-chloro-2,4-dinitrobenzene, which is the most common substrate used to detect GST activity. Although GST activity has been identified in several nematodes, that activity was detected using 1-chloro-2,4-dinitrobenzene, and the enzymes responsible for the activity were not of the size expected for MIFs. To the inventors' knowledge MIF homologues have not yet been identified in any parasitic helminth; efforts to do so have so far proven unsuccessful.

SUMMARY OF THE INVENTION

The present invention relates to parasitic helminth macrophage migration inhibitory factor (MIF) proteins; to parasitic helminth MIF nucleic acid molecules, including those that encode such proteins; to antibodies raised against such proteins (anti-parasitic helminth MIF antibodies); and to compounds that inhibit parasitic helminth MIF activity (i.e, inhibitory compounds or inhibitors). The present invention also includes methods to obtain such proteins, nucleic acid molecules, antibodies and inhibitory compounds. Also included in the present invention are therapeutic compositions comprising such proteins, nucleic acid molecules, antibodies, and/or inhibitory compounds, as well as use of such therapeutic compositions to protect animals from diseases caused by parasitic helminths.

One embodiment of the present invention is an isolated nucleic acid molecule that hybridizes under stringent hybridization conditions with a *Dirofilaria immitis* macrophage migration inhibitory factor (MIF) gene (i.e., a *D. immitis* MIF gene) and/or with an *Onchocerca volvulus* MIF gene (i.e., an *O. volvulus* MIF gene). A *D. immitis* MIF gene preferably includes nucleic acid SEQ ID NO:17 and/or SEQ ID NO:19, and an *O. volvulus* MIF gene preferably includes nucleic acid sequence SEQ ID NO:6 and/or SEQ ID NO:9. A MIF nucleic acid molecule of the present invention can include a regulatory region of a parasitic helminth MIF gene and/or can encode a parasitic helminth MIF protein. Particularly preferred MIF nucleic acid molecules include nucleic acid sequence SEQ ID NO:1, SEQ ID NO:3) SEQ ID NO:4, SEQ ID NO:6, SEQ ID NO:7, SEQ ID NO:9, SEQ ID NO:10, SEQ ID NO:12, SEQ ID NO:16, SEQ ID NO:17, SEQ ID NO:18, SEQ ID NO:19 and/or complements of those SEQ ID NOs, as well as allelic variants of one or more of those nucleic acid molecules.

The present invention also relates to recombinant molecules, recombinant viruses and recombinant cells that include parasitic helminth MIF nucleic acid molecules of the present invention. Also included are methods to produce such nucleic acid molecules, recombinant molecules, recombinant viruses and recombinant cells.

Another embodiment of the present invention includes a parasitic helminth macrophage migration inhibitory factor (MIF) protein (i.e., a parasitic helminth MIF protein) or a protein that includes a parasitic helminth MIF protein. A preferred parasitic helminth MIF protein, when administered to an animal, is capable of eliciting an immune response against a natural parasitic helminth MIF protein. Particularly preferred MIF proteins are proteins that include amino acid sequence SEQ ID NO:2, SEQ ID NO:5, SEQ ID NO:8 and/or SEQ ID NO:11, as well as proteins that are encoded by nucleic acid molecules that are allelic variants of the nucleic acid molecules that encode proteins having SEQ ID NO:2, SEQ ID NO:5, SEQ ID NO:8 and/or SEQ ID NO:11.

The present invention also relates to mimetopes of parasitic helminth MIF proteins as well as to isolated antibodies that selectively bind to parasitic helminth MIF proteins or mimetopes thereof. Also included are methods, including recombinant methods, to produce proteins, mimetopes and antibodies of the present invention.

Another embodiment of the present invention is a method to identify a compound capable of inhibiting MIF activity of a parasitic helminth. The method includes the steps of: (a) contacting an isolated parasitic helminth MIF protein with a putative inhibitory compound under conditions in which, in the absence of the compound, the protein has MIF activity; and (b) determining if the putative inhibitory compound inhibits the MIF activity. Also included in the present invention is a test kit to identify a compound capable of inhibiting MIF activity of a parasitic helminth. Such a test kit includes an isolated parasitic helminth MIF protein having MIF activity and a means for determining the extent of inhibition of that activity in the presence of a putative inhibitory compound.

Yet another embodiment of the present invention is a therapeutic composition that is capable of protecting an animal from disease caused by a parasitic helminth. Such a therapeutic composition includes one or more of the following protective compounds: an isolated parasitic helminth MIF protein or a mimetope thereof, an isolated nucleic acid molecule that hybridizes under stringent hybridization conditions with a *D. immitis* MIF gene and/or an *O. volvulus* MIF gene, an isolated antibody that selectively binds to a parasitic helminth MIF protein, and/or an inhibitor of MIF protein activity identified by its ability to inhibit parasitic helminth MIF activity. A preferred therapeutic composition of the present invention also includes an excipient, an adjuvant and/or a carrier. Preferred MIF nucleic acid molecule compounds of the present invention include naked nucleic acid vaccines, recombinant virus vaccines and recombinant cell vaccines. Also included in the present invention is a method to protect an animal from disease caused by a parasitic helminth. The method includes the step of administering to the animal a therapeutic composition of the present invention.

Suitable parasitic helminths to use in the production (e.g., recombinant, natural, or synthetic production) of nucleic acid molecules, proteins, antibodies and inhibitory compounds of the present invention include nematodes, cestodes and trematodes, with nematodes (such as filariid, ascarid, strongyle and trichostrongyle nematodes) being preferred, with filariids being more preferred, and with *D. immitis* and *O. volvulus* being even more preferred.

Suitable and preferred parasitic helminths from which to protect animals are as disclosed for use in the production of nucleic acid molecules, proteins, antibodies and inhibitory compounds of the present invention. As such, preferred diseases from which to protect animals include diseases caused by nematodes, cestodes and/or trematodes, with diseases caused by nematodes being more preferred targets, and with diseases caused by filariids being even more preferred targets. Particularly preferred diseases from which to protect animals include heartworm and onchocerciasis.

DETAILED DESCRIPTION OF THE INVENTION

The present invention includes the surprising discovery that parasitic helminths produce a macrophage migration inhibitory factor that, although reported for mammals and birds, has not been reported for parasitic helminths. This parasitic helminth protein, also referred to herein as a parasitic helminth macrophage migration inhibitory factor protein, or MIF protein, has utility because it represents a novel target for anti-parasite vaccines and drugs, particularly since a *D. immitis* MIF nucleic acid molecule can encode a protein that binds to immune dog serum; details of isolation of such a *D. immitis* MIF nucleic acid molecule are disclosed in the Examples section. While not being bound by theory, it is believed that parasitic helminth MIF proteins have a role in immune evasion, by, for example, detoxifying compounds harmful to the parasite and/or blocking recruitment of macrophage to the location of the parasite. For example, the potential GST activity of MIF could be used enzymatically in minimizing the effect of electrophilic attack on the extracellular parasite, since GST is known to catalyze the conjugation of glutathione to electrophilic compounds, rendering them nontoxic. Furthermore, the inventors have discovered MIF to be expressed in both *D. immitis* larvae and *O. volvulus* adults, which are both migrating forms of the parasites, suggesting that MIF plays a role in preventing recruitment of macrophage and other effector cells to the proximity of the larvae and adult parasites residing in and migrating through the skin and tissue. Such parasite activities could otherwise induce an inflammatory response harmful to the parasite.

The present invention includes not only parasitic helminth MIF proteins but also parasitic helminth MIF nucleic acid molecules, antibodies directed against parasitic helminth MIF proteins and other inhibitors of MIF proteins. Also included is the use of these proteins, nucleic acid molecules, antibodies and other inhibitors as therapeutic compositions to protect animals from parasitic helminth diseases as well as in other applications, such as those disclosed below.

One embodiment of the present invention is an isolated protein comprising a parasitic helminth MIF protein. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis. As used herein, a helminth MIF protein can be a full-length protein or any homologue of such a protein. Examples of MIF homologues include MIF proteins in which amino acids have been deleted (e.g., a truncated version of the protein, such as a peptide), inserted, inverted, substituted and/or derivatized (e.g., by glycosylation, phosphorylation, acetylation, myristylation, prenylation, palmitoylation, amidation and/or addition of glycerophosphatidyl inositol) such that the homologue includes at least one epitope capable of eliciting an immune response against a parasitic helminth MIF protein. That is, when the homologue is administered to an animal as an immunogen, using techniques known to those skilled in the art, the animal will produce a humoral and/or cellular immune response against at least one epitope of a parasitic helminth MIF protein. The ability of a protein to effect an immune response, can be measured using techniques known to those skilled in the art. MIF protein homologues of the present invention also include MIF proteins that bind to glutathione (i.e., have glutathione binding activity) and/or that selectively bind to immune serum. Examples of methods to measure such activities are disclosed herein, and are known to those skilled in the art. As used herein, the term "selectively binds to" immune serum refers to the ability of isolated proteins and mimetopes thereof to bind to serum collected from animals that are immune to parasitic helminth infection but essentially not to bind, according to standard detection techniques, to serum collected from animals that are not immune to parasitic helminth infection. Preferably, such isolated proteins and mimetopes are able to bind to anti-parasitic helminth immune serum with high affinity.

Methods to produce and use immune serum are disclosed, for example, in Grieve et al., PCT Publication No. WO 94/15593, published Jul. 21, 1994; this reference (also referred to herein as WO 94/15593) is incorporated by reference herein in its entirety.

Parasitic helminth MIF protein homologues can be the result of natural allelic variation or natural mutation. MIF protein homologues of the present invention can also be produced using techniques known in the art including, but not limited to, direct modifications to the protein or modifications to the gene encoding the protein using, for example, classic or recombinant DNA techniques; to effect random or targeted mutagenesis.

Isolated proteins of the present invention, including homologues, can be identified in a straight-forward manner by the proteins' ability to elicit an immune response against parasitic helminth MIF proteins, to bind to glutathione and/or to selectively bind to immune serum.

Isolated proteins of the present invention have the further characteristic of being encoded by nucleic acid molecules that hybridize under stringent hybridization conditions to at least one of the following genes: (a) a gene encoding a *Dirofilaria immitis* MIF protein (i.e., a *D. immitis* MIF gene); and (b) a gene encoding an *Onchocerca volvulus* MIF protein (i.e., an *O. volvulus* MIF gene. It is to be noted that the term "a" or "an" entity refers to one or more of that entity; for example, a gene refers to one or more genes or at least one gene. As such, the terms "a" (or "an"), "one or more" and "at least one" can be used interchangeably herein. It is also to be noted that the terms "comprising", "including", and "having" can be used interchangeably.

As used herein, stringent hybridization conditions refer to standard hybridization conditions under which nucleic acid molecules, including oligonucleotides, are used to identify molecules having similar nucleic acid sequences. Stringent hybridization conditions typically permit isolation of nucleic acid molecules having at least about 70% nucleic acid sequence identity with the nucleic acid molecule being used as a probe in the hybridization reaction. Such standard conditions are disclosed, for example, in Sambrook et al., 1989, *Molecular Cloning: A Laboratory Manual,* Cold Spring Harbor Labs Press. The reference Sambrook et al., ibid., is incorporated by reference herein in its entirety. Examples of such conditions include, but are not limited to, the following: oligonucleotide probes of about 18–25 nucleotides in length with $T_m$'s ranging from about 50° C. to about 65° C., for example, can be hybridized to nucleic acid molecules typically immobilized on a filter (e.g., nitrocellulose filter) in a solution containing 5×SSPE, 1% Sarkosyl, 5×Denhardts and 0.1 mg/ml denatured salmon sperm DNA at 37° C. for about 2 to 12 hours. The filters are then washed 3 times in a wash solution containing 5×SSPE, 1% Sarkosyl at 37° C. for 15 minutes each. The filters can be further washed in a wash solution containing 2×SSPE, 1% Sarkosyl at 37° C. for 15 minutes per wash. Randomly primed DNA probes can be hybridized, for example, to nucleic acid molecules typically immobilized on a filter (e.g., nitrocellulose filter) in a solution containing 5×SSPE, 1% Sarkosyl, 0.5% Blotto (dried milk in water), and 0.1 mg/ml denatured salmon sperm DNA at 42° C. for about 2 to 12 hours. The filters are then washed 2 times in a wash solution containing 5×SSPE, 1% Sarkosyl at 42° C. for 15 minutes each, followed by 2 washes in a wash solution containing 2×SSPE, 1% Sarkosyl at 42° C. for 15 minutes each.

As used herein, a *D. immitis* MIF gene includes all nucleic acid sequences related to a natural *D. immitis* MIF gene such as regulatory regions that control production of the *D. immitis* MIF protein encoded by that gene (such as, but not limited to, transcription, translation or post-translation control regions) as well as the coding region itself. In one embodiment, a *D. immitis* MIF gene of the present invention includes the nucleic acid sequence SEQ ID NO:17 as well as the complement of SEQ ID NO:17. Nucleic acid sequence SEQ ID NO:17 represents the deduced sequence of the coding strand of the apparent coding region of a cDNA (complementary DNA) nucleic acid molecule denoted herein as nDiMIF(1)$_{355}$, the production of which is disclosed in the Examples. The complement of SEQ ID NO:17 refers to the nucleic acid sequence of the strand complementary to the strand having SEQ ID NO:17, which can easily be determined by those skilled in the art. Likewise, a nucleic acid sequence complement of any nucleic acid sequence of the present invention refers to the nucleic acid sequence of the nucleic acid strand that is complementary to (i.e., can form a double helix with) the strand for which the sequence is cited. It should be noted that since nucleic acid sequencing technology is not entirely error-free, SEQ ID NO:17 (as well as other nucleic acid and protein sequences presented herein), at best, represents an apparent nucleic acid sequence of the nucleic acid molecule encoding a *D. immitis* MIF protein of the present invention.

In another embodiment, a *D. immitis* MIF gene can be an allelic variant that includes a similar but not identical sequence to SEQ ID NO:17. An allelic variant of a *D. immitis* MIF gene including SEQ ID NO:17 is a gene that occurs at essentially the same locus (or loci) in the genome as the gene including SEQ ID NO:17, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given parasitic helminth since the genome is diploid and/or among a group of two or more parasitic helminths. An example of an allelic variant of the *D. immitis* MIF gene including SEQ ID NO:17 is a *D. immitis* MIF gene including SEQ ID NO:19. Nucleic acid sequence SEQ ID NO:19 represents the deduced sequence of the coding strand of the apparent coding region of a cDNA nucleic acid molecule denoted herein as nDiMIF(2)$_{333}$, the production of which is disclosed in the Examples. As such, one embodiment of the present invention is a *D. immitis* MIF gene that includes the nucleic acid sequence SEQ ID NO:19 as well as the complement of SEQ ID NO:19.

Similarly, an *O. volvulus* MIF gene includes all nucleic acid sequences related to a natural *O. volvulus* MIF gene such as regulatory regions that control production of the *O. volvulus* MIF protein encoded by that gene as well as the coding region itself. In one embodiment, an *O. volvulus* MIF gene includes the nucleic acid sequence SEQ ID NO:6. Nucleic acid sequence SEQ ID NO:6 represents the deduced sequence of the coding strand of the apparent coding region of a cDNA nucleic acid molecule denoted herein as nOvMIF(1)$_{440}$, the production of which is disclosed in the Examples. In another embodiment, an *O. volvulus* MIF gene can be an allelic variant that includes a similar but not identical sequence to SEQ ID NO:6. An example of such an allelic variant is an *O. volvulus* MIF gene including SEQ ID NO:9. Nucleic acid sequence SEQ ID NO:9 represents the deduced sequence of the coding strand of the apparent coding region of a cDNA nucleic acid molecule denoted herein as nOvMIF(2)$_{522}$, the production of which is disclosed in the Examples.

The minimal size of a MIF protein homologue of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a MIF protein homologue of the present invention is from about 12 to about 18 nucleotides in length.

There is no limit, other than a practical limit, on the maximal size of such a nucleic acid molecule in that the nucleic acid molecule can include a portion of a gene, an entire gene, or multiple genes, or portions thereof. Similarly, the minimal size of a MIF protein homologue of the present invention is from about 4 to about 6 amino acids in length, with preferred sizes depending on whether a full-length, fusion, multivalent, or functional portions of such proteins are desired.

Parasitic helminth MIF proteins of the present invention, including homologues thereof, preferably are capable of eliciting an immune response against a parasitic helminth MIF protein and/or of selectively binding to immune serum. The minimum size of such a protein is a minimum size sufficient to form an epitope, a size that typically is at least from about 5 to about 9 amino acids. As is appreciated by those skilled in the art, an epitope can include amino acids that naturally are contiguous to each other as well as amino acids that, due to the tertiary structure of the natural protein, are in sufficiently close proximity to form an epitope.

One embodiment of the present invention includes a parasitic helminth MIF protein that binds to glutathione and, as such, includes a glutathione-binding domain. Such a glutathione-binding domain is believed to be located primarily in the N-terminal portion of a full-length MIF protein of the present invention. Methods to detect glutathione binding and to identify glutathione binding domains are described, for example, in Blocki et al., 1993, ibid. and references cited therein.

Suitable parasitic helminths from which to isolate parasitic helminth MIF proteins of the present invention (including isolation of the natural protein or production of the protein by recombinant or synthetic techniques) include nematodes, cestodes, and trematodes, with nematodes being preferred. Preferred nematodes from which to isolate MIF proteins include filariid, ascarid, strongyle and trichostrongyle nematodes. Particularly preferred nematodes are those of the genera Acanthocheilonema, Aelurostrongylus, Ancylostoma, Angiostrongylus, Ascaris, Brugia, Bunostomum, Dictyocaulus, Dioctophyme, Dipetalonema, Dirofilaria, Dracunculus, Filaroides, Lagochilascaris, Loa, Mansonella, Muellerius, Necator, Onchocerca, Parafilaria, Parascaris, Protostrongylus, Setaria, Stephanofilaria, Strongyloides, Strongylus, Thelazia, Toxascaris, Toxocara, Trichinella, Uncinaria and Wuchereria. Other particularly preferred nematodes include parasitic helminths of the genera Capillaria, Chabertia, Cooperia, Enterobius, Haemonchus, Nematodirus, Oesophagostomum, Ostertagia, Trichostrongylus and Trichuris. Preferred filariid nematodes include Dirofilaria, Onchocerca, Acanthocheilonema, Brugia, Dipetalonema, Loa, Parafilaria, Setaria, Stephanofilaria and Wuchereria filariid nematodes. Particularly preferred parasitic helminths are nematodes of the genera Dirofilaria and Onchocerca, with *D. immitis,* the parasite that causes heartworm, and *O. volvulus,* the parasite that causes onchocerciasis, being even more preferred.

A preferred parasitic helminth MIF protein of the present invention is a compound that when administered to an animal in an effective manner, is capable of protecting that animal from disease caused by a parasitic helminth. As such, the parasitic helminth is essentially incapable of causing disease in an animal that is immunized with an isolated protein of the present invention. In accordance with the present invention, the ability of a MIF protein of the present invention to protect an animal from disease by a parasitic helminth refers to the ability of that protein to treat, ameliorate and/or prevent disease, including infection leading to disease, caused by the parasitic helminth, preferably by eliciting an immune response against the parasitic helminth. Such an immune response can include humoral and/or cellular immune responses.

Suitable parasites to target include any parasite that is essentially incapable of causing disease in an animal administered a MIF protein of the present invention. As such, a parasite to target includes any parasite that produces a protein having one or more epitopes that can be targeted by a humoral and/or cellular immune response against a MIF protein of the present invention and/or that can be targeted by a compound that otherwise inhibits MIF activity (e.g., a compound that inhibits glutathione binding and/or GST activity), thereby resulting in the reduced ability of the parasite to cause disease in an animal. Suitable and preferred parasites to target include those parasitic helminths disclosed above as being useful in the production of parasitic helminth proteins of the present invention.

It is to be appreciated that the present invention also includes mimetopes of MIF proteins of the present invention that can be used in accordance with methods as disclosed for MIF proteins of the present invention. As used herein, a mimetope of a MIF protein of the present invention refers to any compound that is able to mimic the activity of such a MIF protein, often because the mimetope has a structure that mimics the MIF protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of the isolated protein of the present invention is a fusion protein that includes a parasitic helminth MIF protein-containing domain attached to a fusion segment. Inclusion of a fusion segment as part of a MIF protein of the present invention can enhance the protein's stability during production, storage and/or use. Depending on the segment's characteristics, a fusion segment can also act as an immunopotentiator to enhance the immune response mounted by an animal immunized with a parasitic helminth MIF protein containing such a fusion segment. Furthermore, a fusion segment can function as a tool to simplify purification of a parasitic helminth MIF protein, such as to enable purification of the resultant fusion protein using affinity chromatography. A suitable fusion segment can be a domain of any size that has the desired function (e.g., imparts increased stability, imparts increased immunogenicity to a protein, and/or simplifies purification of a protein). It is within the scope of the present invention to use one or more fusion segments. Fusion segments can be joined to amino and/or carboxyl termini of the MIF-containing domain of the protein. Linkages between fusion segments and MIF-containing domains of fusion proteins can be susceptible to cleavage in order to enable straight-forward recovery of the MIF-containing domains of such proteins. Fusion proteins are preferably produced by culturing a recombinant cell transformed with a fusion nucleic acid molecule that encodes a protein including the fusion segment attached to either the carboxyl and/or amino terminal end of a MIF-containing domain.

Preferred fusion segments for use in the present invention include a metal binding domain, such as a poly-histidine segment capable of binding to a divalent metal ion; an immunoglobulin binding domain, such as Protein A, Protein G, T cell, B cell, Fc receptor or complement protein antibody-binding domains; a sugar binding domain such as a maltose binding domain from a maltose binding protein; and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. An example of a particularly preferred fusion protein of the present invention is PHIS-PDiMIF(1)$_{115}$, production of which is disclosed herein.

Another embodiment of the present invention includes a parasitic helminth MIF protein that also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent.

Examples of multivalent protective compounds include, but are not limited to, a MIF protein of the present invention attached to one or more compounds protective against one or more other infectious agents, particularly an agent that infects humans, cats, dogs, cattle and/or horses, such as, but not limited to: viruses (e.g., caliciviruses, distemper viruses, hepatitis viruses, herpesviruses, immunodeficiency viruses, infectious peritonitis viruses, leukemia viruses, panleukopenia viruses, parvoviruses, rabies viruses, other cancer-causing or cancer-related viruses); bacteria (e.g., Leptospira, Bartonella); fungi and fungal-related microorganisms (e.g., Candida, Cryptococcus, Histoplasma); and other parasites (e.g., Babesia, Cryptosporidium, Eimeria, Encephalitozoon, Hepatozoon, Isospora, Leishmania, Microsporidia, Neospora, Nosema, Plasmodium, Pneumocystis, Toxoplasma, as well as helminth parasites, such as those disclosed herein). In one embodiment, a *D. immitis* MIF protein of the present invention is attached to one or more additional compounds protective against heartworm. In another embodiment, an *O. volvulus* MIF protein of the present invention is attached to one or more additional compounds protective against onchocerciasis.

A preferred isolated protein of the present invention is a protein encoded by a nucleic acid molecule that hybridizes under stringent hybridization conditions with nucleic acid molecules nDiMIF(1)$_{345}$, nDiMIF(2)$_{330}$, nOvMIF(1)$_{345}$, and/or nOvMIF(2)$_{342}$. A further preferred isolated protein is encoded by a nucleic acid molecule that hybridizes under stringent hybridization conditions with a nucleic acid molecule having nucleic acid sequence SEQ ID NO:3 (i.e., SEQ ID NO:17 or SEQ ID:19), SEQ ID NO:6 and/or SEQ ID NO:9.

Translation of SEQ ID NO:1 suggests that nucleic acid molecules nDiMIF(1)$_{532}$ and nDiMIF(2)$_{532}$ each encodes a full-length *D. immitis* MIF protein of about 115 amino acids, referred to herein as PDiMIF(1)$_{115}$, and PDiMIF(2)$_{115}$, respectively, assuming an open reading frame having an initiation (start) codon spanning from about nucleotide 8 through about nucleotide 10 of SEQ ID NO:1 and a termination (stop) codon spanning from about nucleotide 353 through about nucleotide 355 of SEQ ID NO:1. Note that PDiMIF(1)$_{115}$ and PDiMIF(2)$_{115}$ have the same amino acid sequence, and as such, are both referred to herein as PDiMIF(1)$_{115}$. The open reading frame, excluding the stop codon, corresponding to nDiMIF(1)$_{532}$ comprises nucleic acid molecule nDiMIF(1)$_{345}$ of the present invention, the nucleic acid sequence of which is represented herein by SEQ ID NO:17. The open reading frame, excluding the stop codon, corresponding to nDiMIF(2)$_{532}$ comprises nucleic acid molecule nDiMIF(2)$_{330}$ of the present invention, the nucleic acid sequence of which is represented herein by SEQ ID NO:19. SEQ ID NO:3 represents a composite of SEQ ID NO:17 and SEQ ID NO:19. SEQ ID NO:19 is truncated at the 5' end compared to SEQ ID NO:17 and also differs internally in sequence by one nucleotide, as described in more detail in the Examples section.

SEQ ID NO:3 and SEQ ID NO:17 encode proteins having the same amino acid sequence, and as such, each of those proteins is referred to as PDiMIF(1)$_{115}$. SEQ ID NO:19, being truncated, encodes a protein of 110 amino acids referred to herein as PDiMIF(2)$_{110}$. The deduced amino acid sequence of PDiMIF(1)$_{115}$ is represented herein as SEQ ID NO:2. The deduced amino acid sequence of PDiMIF(2)$_{110}$ corresponds to amino acids 6 through 115 of SEQ ID NO:2, since the codons at which the nucleotide difference between SEQ ID NO:17 and SEQ ID NO:19 occurs encode the same amino acid. Based on that amino acid sequence, PDiMIF(1)$_{115}$ has an estimated molecular weight of about 12.3 kD and an estimated pI of about 8.3. The amino acid sequence of PDiMIF(1)$_{115}$ also contains 3 potential N-glycosylation sites.

Comparison of amino acid sequence SEQ ID NO:2 (i.e., the amino acid sequence of PDiMIF(1)$_{115}$) with MIF amino acid sequences reported in GenBank indicates that SEQ ID NO:2 is about 52–53% identical to human MIF and about 55% identical to chicken MIF.

Translation of SEQ ID NO:4 suggests that nucleic acid molecule nOvMIF(1)$_{440}$ encodes a full-length *O. volvulus* MIF protein of about 115 amino acids, referred to herein as POvMIF(1)$_{115}$, assuming an open reading frame having an initiation (start) codon spanning from about nucleotide 8 through about nucleotide 10 of SEQ ID NO:1 and a termination (stop) codon spanning from about nucleotide 353 through about nucleotide 355 of SEQ ID NO:4. The open reading frame, excluding the stop codon, comprises nucleic acid molecule nOvMIF(1)$_{345}$ of the present invention, the nucleic acid sequence of which is represented herein by SEQ ID NO:6. The deduced amino acid sequence of POvMIF(1)$_{115}$ is represented herein as SEQ ID NO:5. Based on that amino acid sequence, POvMIF(1)$_{115}$ has an estimated molecular weight of about 12.24 kD and an estimated pI of about 9.21 The amino acid sequence of POvMIF(1)$_{115}$ also contains 3 potential N-glycosylation sites.

Translation of SEQ ID NO:7 suggests that nucleic acid molecule nOvMIF(2)$_{522}$ encodes a protein of about 114 amino acids, denoted POvMIF(2)$_{114}$, assuming a stop codon spanning from about nucleotide 343 through about nucleotide 345 of SEQ ID NO:7. The amino acid sequence of POvMIF(2)$_{114}$ is represented herein as SEQ ID NO:8. The open reading frame encoding POvMIF(2)$_{115}$ is referred to herein as nOvMIF(2)$_{342}$, the nucleic acid sequence of which is represented in SEQ ID NO:9.

SEQ ID NO:4 and SEQ ID NO:7 are allelic variants and are identical in their coding regions (i.e., SEQ ID NO:6 and SEQ ID NO:9, respectively), except that (a) SEQ ID NO:7 apparently lacks a start codon; (b) SEQ ID NO:7 is about 10 nucleotides shorter than SEQ ID NO:4 at the 5' end; and (c) the region spanning from about nucleotide 1 through about nucleotide 19 of SEQ ID NO:7 is only about 47% identical to the region spanning from about nucleotide 10 through about nucleotide 29 of SEQ ID NO:4.

Comparison of apparent full-length *D. immitis* and *O. volvulus* MIF proteins (i.e., PDiMIF(1)$_{115}$ and POvMIF(1)$_{115}$) indicated that the two MIF proteins were about 88% identical at the amino acid level. Comparison of amino acid sequence SEQ ID NO:5 (i.e., the amino acid sequence of POvMIF(1)$_{115}$) with amino acid sequences reported in GenBank indicates that SEQ ID NO:5, showed some homology to macrophage migration inhibition factor proteins of mammalian and avian origins. The highest scoring match, i.e., 44% identity,, was found between SEQ ID NO:5 and human and bovine MIFs. SEQ ID NO:5 was about 43% identical to rat, mouse and chicken MIFs.

Preferred parasitic helminth MIF proteins of the present invention include: proteins comprising amino acid sequences that are at least about 60%, preferably at least about 70%, and more preferably at least about 80%, and even more preferably at least about 85% identical to amino acid sequences SEQ ID NO:2, SEQ ID NO:5 and/or SEQ ID NO:8. Particularly preferred are proteins comprising amino acid sequences that are at least about 90% and more particularly at least about 95% identical to amino acid sequences SEQ ID NO:2, SEQ ID NO:5 and/or SEQ ID NO:8. More preferred parasitic helminth MIF proteins of the present invention include: proteins encoded by at least a portion of SEQ ID NO:1 and, as such, have amino acid sequences that include at least a portion of SEQ ID NO:2; proteins encoded by at least a portion of SEQ ID NO:4 and, as such, have amino acid sequences that include at least a portion of SEQ ID NO:5; and proteins encoded by at least a portion of SEQ ID NO:7 and, as such, have amino acid sequences that include at least a portion of SEQ ID NO:8.

Particularly preferred parasitic helminth proteins of the present invention are proteins that include SEQ ID NO:2, SEQ ID NO:5, and/or SEQ ID NO:8 (including, but not limited to the encoded proteins, full-length proteins, processed proteins, fusion proteins and multivalent proteins) as well as proteins that are truncated homologues of proteins that include SEQ ID NO:2, SEQ ID NO:5, and/or SEQ ID NO:8. Even more preferred proteins include PDiMIF(1)$_{115}$, PDiMIF(2)$_{110}$, PDiMIF$_{34}$, PHIS-PDiMIF(1)$_{115}$, BvPDiMIF (1)$_{115}$, POvMIF(1)$_{115}$ and POvMIF(2)$_{114}$. Examples of methods to produce such proteins are disclosed herein, including in the Examples section.

Another embodiment of the present invention is an isolated nucleic acid molecule that hybridizes under stringent hybridization conditions with a MIF gene selected from the group consisting of a *D. immitis* MIF gene and an *O. volvulus* MIF gene. The identifying characteristics of such genes are heretofore described. A nucleic acid molecule of the present invention can include an isolated natural parasitic helminth MIF gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with one of the aforementioned genes under stringent hybridization conditions. Suitable and preferred parasitic helminths are disclosed above.

In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated parasitic helminth MIF nucleic acid molecule of the present invention can be obtained from its natural source either as an entire (i.e., complete) gene or a portion thereof capable of forming a stable hybrid with that gene. An isolated parasitic helminth MIF nucleic acid molecule can also be produced using recombinant DNA technology (e.g., polymerase chain reaction (PCR) amplification, cloning) or chemical synthesis. Isolated parasitic helminth MIF nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a parasitic helminth MIF protein of the present invention or to form stable hybrids under stringent conditions with natural gene isolates.

A parasitic helminth MIF nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., ability to elicit an immune response against at least one epitope of a parasitic helminth MIF protein, ability to selectively bind to immune serum, ability to bind to glutathione) and/or by hybridization with a *D. immitis* MIF gene and/or with an *O. volvulus* MIF gene.

An isolated nucleic acid molecule of the present invention can include a nucleic acid sequence that encodes at least one parasitic helminth MIF protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a parasitic helminth MIF protein. As heretofore disclosed, parasitic helminth MIF proteins of the present invention include, but are not limited to, proteins having full-length parasitic helminth MIF coding regions, proteins having partial parasitic helminth MIF coding regions, fusion proteins, multivalent protective proteins and combinations thereof.

A preferred nucleic acid molecule of the present invention, when administered to an animal, is capable of protecting that animal from disease caused by a parasitic helminth. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein, the nucleic acid molecule being delivered to the animal by direct injection (i.e, as a naked nucleic acid) or in a vehicle such as a recombinant virus vaccine or a recombinant cell vaccine.

One embodiment of the present invention is a parasitic helminth MIF nucleic acid molecule that hybridizes under stringent hybridization conditions with nucleic acid molecule nDiMIF(1)$_{532}$, nDiMIF(2)$_{532}$, nOvMIF(1)$_{440}$, and/or nucleic acid molecule nOvMIF(2)$_{522}$. Such parasitic helminth nucleic acid molecules can hybridize under stringent hybridization conditions with a nucleic acid molecule having nucleic acid sequence SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:16, SEQ ID NO:17, SEQ ID NO:18, SEQ ID NO:19, and/or a complement of any of those nucleic acid sequences. The determination of such nucleic acid sequences is described herein, including in the Examples section. It is to be noted, as above, that a double-stranded nucleic acid molecule of the present invention for which a nucleic acid sequence has been determined for one strand that is represented by a SEQ ID NO also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO.

Comparison of nucleic acid molecules containing *D. immitis* and *O. volvulus* MIF coding regions (e.g., nDiMIF (1)$_{345}$ and nOvMIF(1)$_{345}$) indicate that the two MIF coding regions are about 87% identical at the nucleic acid sequence level. Comparison of such *D. immitis* and *O. volvulus* nucleic acid molecules with nucleic acid sequences of mammalian and avian MIF genes reported in GenBank indicates that the coding regions represented in SEQ ID NO:3 and SEQ ID NO:6 were most similar to those of a chicken migration inhibitory factor gene, being, respectively, about 52% and 51% identical, to the chicken gene.

Preferred parasitic helminth nucleic acid molecules include nucleic acid molecules having a nucleic acid sequence that is at least about 55%, preferably at least about 75%, more preferably at least about 85%, even more preferably at least about 90%, and even more preferably at least about 95% identical to nucleic acid sequence SEQ ID NO:3, SEQ ID NO:6, SEQ ID NO:9, and/or a complement thereof.

A preferred nucleic acid molecule of the present invention includes at least a portion of nucleic acid sequence SEQ ID NO:1, SEQ ID NO:4, SEQ ID NO:7 and/or a complement thereof, that is capable of hybridizing to a D. immitis MIF gene and/or to a O. volvulus MIF gene of the present invention. More preferred are nucleic acid molecules that include a nucleic acid sequence, or the complement thereof, of nucleic acid sequences SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:16, SEQ ID NO:17, SEQ ID NO:18 and/or SEQ ID NO:19, as well as nucleic acid molecules that are allelic variants of nucleic acid molecules that include a nucleic acid sequence, or the complement thereof, of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:16, SEQ ID NO:17, SEQ ID NO:18 and/or SEQ ID NO:19. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound. Particularly preferred nucleic acid molecules include $nDiMIF(1)_{532}$, $nDiMIF(2)_{532}$, $nDiMIF_{282}$, $nDiMIF_{102}$, $nDiMIF(1)_{355}$, $nDiMIF(2)_{333}$, $nDiMIF(1)_{345}$, $nDiMIF(2)_{330}$, $nDiMIF(1)_{348}$, $nBvDiMIF(1)_{348}$, $nRcnDiMIF(1)_{348}$, $nOvMIF(1)_{440}$, $nOvMIF(2)_{522}$, $nOvMIF(1)_{345}$ and/or $nOvMIF(2)_{342}$.

The present invention also includes nucleic acid molecules encoding a protein having at least a portion of SEQ ID NO:2, SEQ ID NO:5, SEQ ID NO:8 and/or SEQ ID NO:11 including nucleic acid molecules that have been modified to accommodate codon usage properties of the cells in which such nucleic acid molecules are to be expressed.

Knowing the nucleic acid sequences of certain parasitic helminth MIF nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain MIF nucleic acid molecules for other parasitic helminths, particularly since, as described in detail in the Examples section, knowledge of *D. immitis* MIF nucleic acid molecules of the present invention enabled the isolation of *O. volvulus* MIF nucleic acid molecules of the present invention. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecule include parasitic helminth L3, L4 or adult libraries as well as genomic DNA libraries. Similarly, preferred DNA sources to screen or from which to amplify nucleic acid molecules include parasitic helminth L3, L4 or adult DNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising parasitic helminth MIF genes or other parasitic helminth MIF nucleic acid molecules. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit MIF protein production or activity. Such therapeutic applications include the use of such oligonucleotides in, for example, antisense-, triplex formation-, ribozyme- and/or RNA drug-based technologies. The present invention, therefore, includes such oligonucleotides and methods to protect animals from disease caused by parasitic helminths by use of one or more of such technologies. Appropriate oligonucleotide-containing therapeutic compositions can be administered to an animal, using techniques known to those skilled in the art, either prior to or after infection by a parasitic helminth such as *D. immitis* or *O. volvulus* in order to protect the animal from disease.

The present invention also includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of parasitic helminth MIF nucleic acid molecules of the present invention. One type of recombinant vector, referred to herein as a recombinant molecule and described in more detail below, can be used in the expression of nucleic acid molecules of the present invention. Preferred recombinant vectors are capable of replicating in the transformed cell.

Suitable and preferred nucleic acid molecules to include in recombinant vectors of the present invention are as disclosed herein for suitable and preferred parasitic helminth MIF nucleic acid molecules per se. Particularly preferred nucleic acid molecules to include in recombinant vectors, and particularly in recombinant molecules, of the present invention include $nDiMIF(1)_{532}$, $nDiMIF(2)_{532}$, $nDiMIF_{282}$, $nDiMIF_{102}$, $nDiMIF(1)_{355}$, $nDiMIF(2)_{333}$, $nDiMIF(1)_{345}$, $nDiMIF(2)_{330}$, $nDiMIF(1)_{348}$, $nBvDiMIF(1)_{348}$, $nRcnDiMIF(1)_{348}$, $nOvMIF(1)_{440}$, $nOvMIF(2)_{522}$, $nOvMIF(1)_{345}$ and $nOvMIF(2)_{342}$.

Isolated proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell that is capable of expressing the protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable and preferred nucleic acid molecules with which to transform a cell are as disclosed herein for suitable and preferred parasitic helminth MIF nucleic acid molecules per se. Particularly preferred nucleic acid molecules to include in recombinant cells of the present invention include $nDiMIF(1)_{532}$, $nDiMIF(2)_{532}$, $nDiMIF_{282}$, $nDiMIF_{102}$, $nDiMIF(1)_{355}$, $nDiMIF(2)_{333}$, $nDiMIF(1)_{345}$, $nDiMIF(2)_{330}$, $nDiMIF(1)_{348}$, $nBvDiMIF(1)_{348}$, $nRcnDiMIF(1)_{348}$, $nOvMIF(1)_{440}$, $nOvMIF(2)_{522}$, $nOvMIF(1)_{345}$ and $nOvMIF(2)_{342}$.

Suitable host cells to transform include any cell that can be transformed with a nucleic acid molecule of the present invention. Host cells can be either untransformed cells or cells that are already transformed with at least one nucleic acid molecule. Host cells of the present invention either can be endogenously (i.e., naturally) capable of producing parasitic helminth MIF proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), insect, other animal and plant cells. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi*; *Salmonella typhimurium*, including attenuated strains such as UK-1 $_{x}$3987 and SR-11 $_{x}$4072; *Spodoptera frugiperda*; *Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells and more preferably in the cell types heretofore disclosed.

Recombinant molecules of the present invention may also (a) contain secretory signals (i.e., signal segment nucleic acid sequences) to enable an expressed parasitic helminth protein of the present invention to be secreted from the cell that produces the protein and/or (b) contain fusion sequences which lead to the expression of nucleic acid molecules of the present invention as fusion proteins. Examples of suitable signal segments and fusion segments encoded by fusion segment nucleic acids are disclosed herein. Eukaryotic recombinant molecules may include intervening and/or untranslated sequences surrounding and/or within the nucleic acid sequences of nucleic acid molecules of the present invention.

Suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments.

Nucleic acid molecules of the present invention can be operatively linked to expression vectors containing regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other parasite, insect and mammalian cells, such as, but not limited to, tac, lac, trp, trc, oxy-pro, omp/lpp, rrnB, bacteriophage lambda (λ) (such as $\lambda.p_L$ and $\lambda p_R$ and fusions that include such promoters), bacteriophage T7, T7lac, bacteriophage T3, bacteriophage SP6, bacteriophage SP01, metallothionein, α-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters, simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a parasitic helminth, such as a *D. immitis* or *O. volvulus* molecule prior to isolation.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. Particularly preferred recombinant molecules include pβgal-nDiMIF$_{282}$, pHis-nDiMIF(1)$_{348}$, pVL1393-nDiMIF(1)$_{348}$, and pKB3poly-nDiMIF(1)$_{348}$, pHis-nOvMIF(1)$_{348}$, pVL1393-nOvMIF(1)$_{348}$, and pKB3poly-nOvMIF(1)$_{348}$. Details regarding the production of *D. immitis* MIF nucleic acid molecule-containing recombinant molecules are disclosed herein. *O. volvulus* MIF recombinant molecules are produced in a similar manner.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein. Particularly preferred recombinant cells include *E. coli*:pβgal-nDiMIF$_{282}$, *E. coli*:pHis-nDiMIF(1)$_{348}$, *S. frugiperda*:pVL1393-nDiMIF(1)$_{348}$, BS-C-1:pKB3poly-nDiMIF(1)$_{348}$, *E. coli*:pHis-nOvMIF(1)$_{348}$, *S. frugiperda*:pVL1393-nOvMIF(1)$_{348}$, and BS-C-1:pKB3poly-nDiMIF(1)$_{348}$. Details regarding the production of these recombinant cells are disclosed herein.

Recombinant cells of the present invention can also be co-transformed with one or more recombinant molecules including parasitic helminth MIF nucleic acid molecules encoding one or more proteins of the present invention and one or more other proteins useful in the production of multivalent vaccines which can include one or more protective compounds.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

In accordance with the present invention, recombinant cells of the present invention can be used to produce one or more proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a parasitic helminth MIF protein of the present invention. Such a medium is typically an aqueous medium comprising assimilable carbon, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and should be capable of stimulating the production of antibodies in a treated animal.

The present invention also includes isolated antibodies capable of selectively binding to a parasitic helminth MIF protein of the present invention or to a mimetope thereof. Such antibodies are also referred to herein as anti-parasitic helminth MIF antibodies. Particularly preferred antibodies of this embodiment include anti-*D. immitis* MIF antibodies and anti-*O. volvulus* MIF antibodies.

Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees.

As used herein, the term "selectively binds to" refers to the ability of antibodies of the present invention to preferentially bind to specified proteins and mimetopes thereof of the present invention. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid. An anti-parasitic helminth MIF antibody preferably binds to a parasitic helminth MIF protein in such a way as to reduce the activity of that protein.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Antibodies of the present invention also include chimeric antibodies that can bind to more than one epitope. Preferred antibodies are raised in response to proteins, or mimetopes thereof, that are encoded, at least in part, by a nucleic acid molecule of the present invention.

A preferred method to produce antibodies of the present invention includes (a) administering to an animal an effective amount of a protein or mimetope thereof of the present invention to produce the antibodies and (b) recovering the antibodies. In another method, antibodies of the present invention are produced recombinantly using techniques as heretofore disclosed to produce parasitic helminth MIF proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic helminths susceptible to treatment by such antibodies, (b) as reagents in assays to detect infection by such helminths and/or (c) as tools to screen expression libraries and/or to recover desired proteins of the present invention from a mixture of proteins and other contaminants. Furthermore, antibodies of the present invention can be used to target cytotoxic agents to parasitic helminths of the present invention in order to directly kill such helminths. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from disease caused by a parasitic helminth. Therapeutic compositions of the present invention include at least one of the following protective compounds: an isolated parasitic helminth MIF protein or a mimetope thereof, an isolated nucleic acid molecule that hybridizes under stringent hybridization conditions with a D. immitis MIF gene and/or an O. volvulus MIF gene, an isolated antibody that selectively binds to a parasitic helminth MIF protein, an inhibitor of MIF protein activity identified by its ability to inhibit parasitic helminth MIF activity, and a mixture thereof (i.e., combination) of at least two of the compounds. As used herein, a protective compound refers to a compound that, when administered to an animal in an effective manner, is able to treat, ameliorate, and/or prevent disease caused by a parasitic helminth of the present invention. Preferred helminths to target are heretofore disclosed. Examples of proteins, nucleic acid molecules, antibodies and inhibitors of the present invention are disclosed herein.

The present invention also includes a therapeutic composition comprising at least one parasitic helminth MIF-based compound of the present invention in combination with at least one additional compound protective against one or more infectious agents. Examples of such compounds and infectious agents are disclosed herein.

Therapeutic compositions of the present invention can be administered to any animal susceptible to such therapy, preferably to mammals, and more preferably to dogs, cats, humans, ferrets, horses, cattle, sheep and other pets, economic food animals and/or zoo animals. Preferred animals to protect against heartworm include dogs, cats, humans and ferrets, with dogs and cats being particularly preferred. Preferred animals to protect against onchocerciasis include humans, cattle and horses, with humans being particularly preferred.

In one embodiment, a therapeutic composition of the present invention can be administered to the vector in which the parasitic helminth develops, such as to a mosquito in order to prevent the spread of heartworm or to a black fly in order to prevent the spread of onchocerciasis. Such administration could be orally or by developing transgenic vectors capable of producing at least one therapeutic composition of the present invention. In another embodiment, a vector, such as a mosquito or a black fly, can ingest therapeutic compositions present in the blood of a host that has been administered a therapeutic composition of the present invention.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the therapeutic composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax™ adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from disease caused by parasitic helminths. The therapeutic composition is preferably released over a period of time ranging from about 1 to about 12 months. A controlled release formulation of the present invention is capable of effecting a treatment for preferably at least about 1 month, more preferably at least about 3 months and even more preferably for at least about 6 months, even more preferably for at least about 9 months, and even more preferably for at least about 12 months.

In order to protect an animal from disease caused by a parasitic helminth of the present invention, a therapeutic composition of the present invention is administered to the animal in an effective manner such that the composition is capable of protecting that animal from a disease caused by a parasitic helminth. For example, an isolated protein or mimetope thereof, when administered to an animal in an effective manner, is able to elicit (i.e., stimulate) an immune response, preferably including both a humoral and cellular response, that is sufficient to protect the animal from the disease. Similarly, an antibody of the present invention, when administered to an animal in an effective manner, is administered in an amount so as to be present in the animal at a titer that is sufficient to protect the animal from the disease, at least temporarily. Oligonucleotide nucleic acid molecules of the present invention can also be administered in an effective manner, thereby reducing expression of parasitic helminth MIF proteins in order to interfere with development of parasitic helminths targeted in accordance with the present invention.

Therapeutic compositions of the present invention can be administered to animals prior to infection in order to prevent infection and/or can be administered to animals after infection in order to treat disease caused by the parasitic helminth. For example, proteins, mimetopes thereof, and antibodies thereof can be used as immunotherapeutic agents.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster vaccinations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme or RNA drug) in the animal to be protected from disease. Nucleic acid molecules can be delivered to an animal in a variety of methods including, but not limited to, (a) administering a naked (i.e., not packaged in a viral coat or cellular membrane) nucleic acid vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A naked nucleic acid vaccine of the present invention includes a nucleic acid molecule of the present invention and preferably includes a recombinant molecule of the present invention that preferably is replication, or otherwise amplification, competent. Such a vaccine can comprise any nucleic acid molecule or recombinant molecule of the present invention. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccines of the present invention can be administered in a variety of ways, with intramuscular, subcutaneous, intradermal, transdermal, intranasal and oral routes of administration being preferred. A preferred single dose of a naked nucleic acid vaccine ranges from about 1 nanogram (ng) to about 100 $\mu$g, depending on the route of administration and/or method of delivery, as can be determined by those skilled in the art. Suitable delivery methods include, for example, by injection, as drops, aerosolized and/or topically. Suitable excipients include, for example, physiologically acceptable aqueous solutions (e.g., phosphate buffered saline as well as others disclosed above), liposomes (including neutral or cationic liposomes), and other lipid membrane-based vehicles (e.g., micelles or cellular membranes).

A recombinant virus vaccine of the present invention includes a recombinant molecule of the present invention that is packaged in a viral coat and that can be expressed in an animal after administration. Preferably, the recombinant molecule is packaging-deficient and/or encodes an attenuated virus. A number of recombinant viruses can be used, including, but not limited to, those based on alphaviruses, poxviruses, adenoviruses, herpesviruses, and retroviruses. Preferred recombinant virus vaccines are those based on alphaviruses (such as Sindbis virus), raccoon poxviruses, species-specific herpesviruses and species-specific poxviruses. An example of methods to produce and use recombinant virus vaccines are disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from disease caused by a parasitic helminths as disclosed herein. For example, a recombinant virus vaccine comprising a *D. immitis* MIF nucleic acid molecule of the present invention is administered according to a protocol that results in the animal producing a sufficient immune response to protect itself from heartworm. A preferred single dose of a recombinant virus vaccine of the present invention is from about $1 \times 10^4$ to about $1 \times 10^7$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, *E. coli,* Listeria, Mycobacterium, *S. frugiperda,* yeast, (including *Saccharomyces cerevisiae*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells or cell lysates.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Such techniques are known to those skilled in the art.

One preferred embodiment of the present invention is the use of parasitic helminth MIF proteins, nucleic acid molecules, antibodies and inhibitory compounds of the present invention, and particularly *D. immitis* MIF proteins, nucleic acid molecules, antibodies and inhibitory compounds of the present invention, to protect an animal from heartworm. It is particularly preferred to prevent L3 larvae that are delivered to the animal by the mosquito intermediate host from maturing into adult worms. As such, preferred therapeutic compositions are those that are able to inhibit at least one step in the portion of the parasite's development cycle that includes L3 larvae, third molt, L4 larvae, fourth molt, immature adult prior to entering the circulatory system. In dogs, this portion of the development cycle is about 70 days. Particularly preferred therapeutic compositions include *D. immitis* MIF-based therapeutic compositions of the present invention, particularly since MIF is expressed in L3 and L4. Such compositions include *D. immitis* MIF nucleic acid molecules, *D. immitis* MIF proteins and mimetopes thereof, anti-*D. immitis* MIF antibodies, and inhibitors of *D. immitis* MIF activity. Such compositions are administered to animals in a manner effective to protect the animals from heartworm. Additional protection may be obtained by administering additional protective compounds, including other *D. immitis* proteins, nucleic acid molecules, antibodies and inhibitory compounds.

Another preferred embodiment of the present invention is the use of parasitic helminth MIF proteins, nucleic acid molecules, antibodies and inhibitory compounds of the present invention, and particularly *O. volvulus* MIF proteins, nucleic acid molecules, antibodies and inhibitory compounds of the present invention, to protect a human from onchocerciasis. It is particularly preferred to prevent L3, L4 and adult worms from evading the immune system of the host. Preferred therapeutic compositions are those that are able to inhibit at least one step in the portion of the parasite's development cycle that includes L3 larvae, third molt, L4 larvae, fourth molt and immature adult prior to entering the subcutaneous tissues. In humans infected with *O. volvulus,* this portion of the development cycle is about 150 days. Additional preferred compounds inhibit adult worm survival. As such, preferred therapeutic compositions include *O. volvulus* MIF-based therapeutic compositions of the present invention. Such compositions include *O. volvulus* MIF nucleic acid molecules, *O. volvulus* MIF proteins and mimetopes thereof, anti-*O. volvulus* MIF antibodies, and inhibitors of *O. volvulus* MIF activity. Such compositions are administered to humans in a manner effective to protect humans from onchocerciasis. Additional protection may be obtained by administering additional protective compounds, including other Onchocerca, preferably *O. volvulus,* proteins, nucleic acid molecules, antibodies, and inhibitory compounds.

One therapeutic composition of the present invention includes an inhibitor of parasitic helminth MIF activity, i.e., a compound capable of substantially interfering with the function of a parasitic helminth MIF susceptible to inhibition by an inhibitor of parasitic helminth MIF activity.

An inhibitor of MIF activity can be identified using parasitic helminth, and preferably *D. immitis* and/or *O. volvulus* MIF proteins of the present invention. One embodiment of the present invention is a method to identify a compound capable of inhibiting MIF activity of a parasitic helminth. Such a method includes the steps of (a) contacting (e.g., combining, mixing) an isolated parasitic helminth MIF protein with a putative inhibitory compound under conditions in which, in the absence of the compound, the protein has MIF activity, and (b) determining if the putative inhibitory compound inhibits the MIF activity. Putative inhibitory compounds to screen include organic molecules, antibodies (including mimetopes thereof) and substrate analogs. Methods to determine MIF activity are known to those skilled in the art; see, for example, citations in background section and references included therein.

The present invention also includes a test kit to identify a compound capable of inhibiting MIF activity of a parasitic helminth. Such a test kit includes an isolated parasitic helminth MIF protein having MIF activity and a means for determining the extent of inhibition of MIF activity in the presence of (i.e., effected by) a putative inhibitory compound. Such compounds are also screened to identify those that are substantially not toxic in host animals.

MIF inhibitors isolated by such a method, and/or test kit, can be used to inhibit any MIF that is susceptible to such an inhibitor. Preferred MIF enzymes to inhibit are those produced by parasitic helminths. A particularly preferred MIF inhibitor of the present invention is capable of protecting an animal from heartworm or onchocerciasis. It is also within the scope of the present invention to use inhibitors of the present invention to target MIF-related disorders in animals. Therapeutic compositions comprising MIF inhibitory compounds of the present invention can be administered to animals in an effective manner to protect animals from disease caused by the targeted MIF enzymes, and preferably to protect animals from heartworm and humans from onchocerciasis. Effective amounts and dosing regimens can be determined using techniques known to those skilled in the art.

It is also within the scope of the present invention to use isolated proteins, mimetopes, nucleic acid molecules and antibodies of the present invention as diagnostic reagents to detect infection by parasitic helminths. Such diagnostic reagents can be supplemented with additional compounds that can detect other phases of the parasite's life cycle. Methods to use such diagnostic reagents to diagnose parasitic helminth infection are well known to those skilled in the art. Suitable and preferred parasitic helminths to detect are those to which therapeutic compositions of the present invention are targeted. Particularly preferred parasitic helminths to detect using diagnostic reagents of the present invention are Dirofilaria and Onchocerca.

The following examples are provided for the purposes of illustration and are not intended to limit the scope of the present invention.

EXAMPLES

Example 1

This Example describes the isolation and sequencing of several $D.$ $immitis$ MIF nucleic acid molecules of the present invention. It is to be noted that the Examples include a number of molecular biology, microbiology, immunology and biochemistry techniques considered to be known to those skilled in the art. Disclosure of such techniques can be found, for example, in Sambrook et al., ibid. and related references.

A. A $D.$ $immitis$ MIF nucleic acid molecule of about 282 nucleotides, denoted nDiMIF$_{282}$, was identified by its ability to encode a protein that selectively bound to at least one component of immune serum collected from a dog immunized with $D.$ $immitis$ larvae. Immune serum was produced and used as described in WO 94/15593, ibid. Specifically, a $D.$ $immitis$ L4 cDNA expression library was constructed in Uni-ZAP™ XR vector (available from Stratagene Cloning Systems, La Jolla, Calif.), using Stratagene's ZAP-cDNA Synthesis Kit protocol and fourth stage (L4) larval mRNAs. Using the protocol described in the Stratagene picoBlue immunoscreening kit, the L4 larval cDNA expression library was screened with immune dog sera, prepared as described in WO 94/15593, ibid. Immunoscreening of duplicate plaque lifts of the cDNA library with the same immune dog serum identified a clone containing nucleic acid molecule nDiMIF$_{252}$.

The plaque-purified clone including $D.$ $immitis$ nucleic acid sequence nDiMIF$_{282}$ was converted into a double stranded recombinant molecule, herein denoted as pβgal-nDiMIF$_{282}$, using ExAssist™ helper phage and SOLR™ $E.$ $coli$ according to the in vivo excision protocol described in the Stratagene ZAP-cDNA Synthesis Kit. Double stranded plasmid DNA was prepared using an alkaline lysis protocol, such as that described in Sambrook et al., ibid. The plasmid DNA was digested with EcoRI and XhoI restriction endonucleases to release a single $D.$ $immitis$ nDiMIF$_{282}$ DNA fragment of about 282 nucleotides in size.

The plasmid containing $D.$ $immitis$ nDiMIF$_{282}$ was sequenced using the Sanger dideoxy chain termination method, as described in Sambrook et al., ibid. An about 282 nucleotide consensus sequence of the entire $D.$ $immitis$ nDiMIF$_{282}$ DNA fragment was determined and is presented as SEQ ID NO:10. The $D.$ $immitis$ nDiMIF$_{282}$ sequence represents a partial cDNA clone truncated on the amino terminus and spans nucleotides from about 251 through about 532 of SEQ ID NO:1 (the production of which is described below). The first stop codon within the $D.$ $immitis$ nDiMIF$_{282}$ sequence spans nucleotides from about 103 through about 105 of SEQ ID NO:10. A putative polyadenylation signal (5' AATAAA 3') is located in a region spanning from about nucleotide 249 through about 254 of SEQ ID NO:10.

Translation of SEQ ID NO:10 yields a protein of about 34 amino acids, denoted PDiMIF$_{34}$, the amino acid sequence of which is presented in SEQ ID NO:11. SEQ ID NO:11 corresponds to about from amino acid 82 through about amino acid 115 of SEQ ID NO:2 (the production of which is described below). The coding region of PDiMIF$_{34}$ is referred to herein as nDiMIF$_{102}$, the nucleic acid sequence of which is represented in SEQ ID NO:12.

B. A $D.$ $immitis$ nDiMIF nucleic acid molecule containing apparently the entire coding region of nDiMIF was produced using the following two primers to amplify, by polymerase chain reaction (PCR), a MIF nucleic acid molecule from a $D.$ $immitis$ L3 cDNA library: (a) a vector sense primer having the nucleic acid sequence 5' CGCTCTAGAAC-TAGTGGATC 3', denoted herein as SEQ ID NO:13; and (b) C3 ant, an antisense primer having nucleic acid sequence 5' CCAATTATCCGAAAGTAGATCC 3', denoted herein as SEQ ID NO:14, that was designed from the complement of the region spanning from about nucleotide 88 through about nucleotide 109 of SEQ ID NO:10 (corresponding to a region spanning from about nucleotide 338 through about nucleotide 359 of SEQ ID NO:1), that region including the first stop codon detected in the $D.$ $immitis$ nDiMIF$_{282}$ sequence. The resultant PCR product of about 355 nucleotides, denoted $D.$ $immitis$ nDiMIF(1)$_{355}$, was cloned into the TA cloning vector (available from Invitrogen, San Diego, Calif.). An antisense probe having the nucleic acid sequence 5' CTTCGGAATTTTCAGCTCATCAGCGAGC 3' (denoted herein as SEQ ID NO:15), representing the complement of nucleotide 6 through about nucleotide 33 of SEQ ID NO:10, was used to verify the authenticity of the $D.$ $immitis$ nDiMIF(1)$_{355}$ PCR product, by hybridization analysis.

The nucleic acid sequence of $D.$ $immitis$ nDiMIF(1)$_{355}$ is presented in SEQ ID NO:16. Translation of SEQ ID NO:16 yields an apparent full-length protein of about 115 amino acids, denoted PDiMIF(1)$_{115}$, the amino acid sequence of which is presented in SEQ ID NO:2. The coding region of PDiMIF(1)$_{115}$ is referred to herein as nDiMIF(1)$_{345}$, the nucleic acid sequence of which is represented in SEQ ID NO:17.

C. A second, independent PCR clone was amplified from the L3 cDNA library with the vector and C3 ant primers and is denoted herein as nDiMIF(2)$_{333}$. The nucleic acid sequence of nDiMIF(2)$_{333}$, which is represented herein as SEQ ID NO:18, differs from that of nDiMIF(1)$_{355}$ (SEQ ID NO:16) by one base: SEQ ID NO:18 contains a T at position 37 (i.e., the position corresponding to position 49 of SEQ ID NO:16) whereas SEQ ID NO:16 contains an A at position 49. As such, nDiMIF(2)$_{333}$ represents an allelic variant of nDiMIF(1)$_{355}$. The deduced amino acid (arginine) encoded by nDiMIF(2)$_{333}$ at position 35–37 was the same as that encoded by the D. immitis nDiMIF(1)$_{355}$ sequence at position 47–49. As such, translation of SEQ ID NO:18 yields a truncated protein of about 110 amino acids, denoted PDiMIF (2)$_{110}$, the amino acid sequence of which corresponds to amino acids 6 through 115 of SEQ ID NO:2. The coding region of PDiMIF(2)$_{110}$ is referred to herein as nDiMIF(2)$_{330}$, the nucleic acid sequence of which is represented in SEQ ID NO:19.

To confirm the D. immitis origin of the isolated MIF cDNA nucleic acid molecules, a Southern blot containing about 10 micrograms of EcoRI restricted Dirofilaria immitis genomic DNA and Aedes aegypti genomic DNA was hybridized under stringent conditions with nDiMIF(2)$_{330}$ DNA radiolabeled by random priming with the Megaprime DNA Labeling System (available from Amersham Life Science, Arlington Heights, Ill.). The probe detected two bands of about 4390 and 1490 nucleotides only in the D. immitis genomic DNA.

D. A deduced nucleic acid sequence combining the sequence information disclosed in Example 1, A–C, is presented in SEQ ID NO:1. SEQ ID NO:1 was determined by combining the unique and common nucleotide sequences from the PCR clones D. immitis nDiMIF(1)$_{355}$, D. immitis nDiMIF(2)$_{333}$, and the cDNA clone D. immitis nDiMIF$_{282}$. As such, SEQ ID NO:1 represents the sequences of two nucleic acid molecules of the present invention, namely D. immitis nDiMIF(1)$_{532}$ and D. immitis nDiMIF(2)$_{532}$. Nucleotides 1–355 and 23–355, respectively, of SEQ ID NO:1 were identified from the D. immitis allelic variant nucleic acid molecules nDiMIF(1)$_{355}$ and nDiMIF(2)$_{333}$. Nucleotides 251 through 532 of SEQ ID NO:1 were identified from D. immitis nucleic acid molecule nDiMIF$_{282}$.

Translation of the entire 532 nucleotides of SEQ ID NO:1 yields a protein of about 115 amino acids, denoted PDiMIF (1)$_{115}$, that has an amino acid sequence as represented in SEQ ID NO:2, assuming the ATG codon spanning nucleotides from about 8 through about 10 of SEQ ID NO:1 is the initiation codon, and that the stop codon is the TAA spanning nucleotides from about 353 through about 355 of SEQ ID NO:1. A putative polyadenylation signal (5' AATAAA 3') is located in a region spanning nucleotides from about 499 through about 504 of SEQ ID NO:1. The amino acid sequence of D. immitis PDiMIF(1)$_{115}$ (i.e., SEQ ID NO:2) predicts that PDiMIF(1)$_{115}$ has an estimated molecular weight of about 12.3 kD and an estimated pI of about 8.3. There are 3 predicted N-glycosylation sites in the PDiMIF (1)$_{115}$ deduced amino acid sequence, which are located in regions spanning amino acids from about 73 through about 75, from about 103 through about 105 and from about 110 through about 112 of SEQ ID NO:2.

A homology search of the non-redundant protein sequence database was performed through the National Center for Biotechnology Information using the BLAST network. This database includes +SwissProt+PIR+ SPUpdate+GenPept+GPUpdate. The search was performed using SEQ ID NO:2 and showed significant homology to macrophage migration inhibition factor proteins of mammalian and avian origins, spanning from about amino acid 1 through about amino acid 115 of SEQ ID NO:2. The highest scoring matches of the homology search at the amino acid level include: Genbank accession number M25639: human macrophage migration inhibitory factor, about 53% identical; C47274: chicken macrophage migration inhibitory factor, about 55% identical; and P80177: human macrophage migration inhibitory factor, about 52% identical. At the nucleotide level, the coding regions represented in SEQ ID NO:3 were most similar to that of chicken macrophage migration inhibitory factor, being about 52% identical.

Example 2

This Example discloses the production of a recombinant cell of the present invention.

Recombinant molecule pHis-nDiMIF(1)$_{348}$, containing D. immitis MIF nucleotides from about 8 through about 355 operatively linked to trc transcription control sequences and to a fusion sequence encoding a poly-histidine segment comprising 6 histidines was produced in the following manner. An about 348-nucleotide DNA fragment containing nucleotides spanning from about 8 through about 355 of SEQ ID NO:16, denoted herein as nDiMIF(1)$_{345}$, was PCR amplified from nucleic acid molecule D. immitis nDiMIF (1)$_{355}$, produced as described in Example 1, using the primers MIF sen 5' GGACGGATCCAATGC- CATATTTCACGATC 3' (denoted herein as SEQ ID NO:20; BamHI site in bold) and MIF ant 5' GAGCGAATTCT- TATCCGAAAGTAGATCC 3' (denoted herein as SEQ ID NO:21; EcoRI site in bold). Recombinant molecule pHis-nDiMIF(1)$_{348}$ was produced by digesting the nDiMIF(1)$_{348}$-containing PCR product with BamHI and EcoRI restriction endonucleases, gel purifying the resulting fragment and directionally subcloning it into expression vector pTrcHisB (available from Invitrogen) that had been cleaved with BamHI and EcoRI and gel purified.

Recombinant molecule pHis-nDiMIF(1)$_{348}$ was transformed into E. coli to form recombinant cell E. coli:pHis-nDiMIF(1)$_{348}$ using standard techniques as disclosed in Sambrook et al., ibid.

Example 3

This Example discloses the production of a MIF protein of the present invention in a prokaryotic cell.

Recombinant cell E. coli:pHis-nDiMIF(1)$_{348}$, produced as described in Example 2, was cultured in shake flasks containing an enriched bacterial growth medium containing 0.1 mg/ml ampicillin and 0.1% glucose at about 32° C. When the cells reached an OD$_{600}$ of about 0.4, expression of D. immitis nDiMIF(1)$_{348}$ was induced by addition of about 0.5 mM isopropyl-β-D-thiogalactoside (IPTG), and the cells were cultured for about 3 hours at about 32° C. Protein production was monitored by SDS PAGE of recombinant cell lysates, followed by Coomassie blue staining, using standard techniques. Recombinant cell E. coli:pHis-nDiMIF (1)$_{348}$ produced a fusion protein, denoted herein as PHIS-PDiMIF(1)$_{115}$, that migrated with an apparent molecular weight of about 16 kD.

Immunoblot analysis of recombinant cell E. coli:pHis-nDiMIF(1)$_{348}$ lysates indicated that the about 16 kD protein was able to bind to a T7 tag monoclonal antibody (available from Novagen, Inc., Madison, Wis.) directed against the fusion portion of the recombinant PHIS-PDiMIF(1)$_{115}$ fusion protein.

The PHIS-PDiMIF(1)$_{115}$ histidine fusion protein was separated from E. coli proteins by nickel chelation chromatography and an imidazole gradient. Immunoblot analysis of the E. coli:pHis-nDiMIF(1)$_{348}$ lysate, column eluate and column void volume indicated that the PHIS-PDiMIF(1)$_{115}$ 16 kD protein isolated using nickel column chromatography was able to selectively bind to a T7 tag monoclonal antibody.

Example 4

This Example describes the production of a MIF protein of the present invention in a eukaryotic cell.

Recombinant molecule pVL1393-nDiMIF(1)$_{348}$, containing a D. immitis MIF nucleic acid molecule spanning nucleotides from about 8 through about 355 of SEQ ID NO:16 operatively linked to baculovirus polyhedron transcription control sequences was produced in the following manner. In order to subclone a MIF nucleic acid molecule into baculovirus expression vectors, a MIF nucleic acid molecule-containing fragment was PCR amplified from D. immitis nDiMIF(1)$_{355}$ DNA (produced as in Example 1), using a sense primer BvMIF sen (5' CGCGGATC-CTATAAATATGCCATATTTCACGATCG 3' (denoted herein as SEQ ID NO:22; BamHI site in bold) and an antisense primer BvMIF ant 5' CCGGAATTCTTATC-CGAAAGTAGATCC 3' (denoted herein as SEQ ID NO:23; EcoRI site in bold). The N-terminal primer (SEQ ID NO:22) was designed from nDiMIF(1)$_{355}$ sequence with modifications to enhance expression in the baculovirus system. The PCR product was digested with BamHI and EcORI to produce nucleic acid molecule nBvDiMIF(1)$_{348}$ and directionally subcloned into the unique BamHI and EcoRI sites of pVL1393 (available from Invitrogen) baculovirus shuttle plasmid to produce recombinant molecule pVL1393-nDiMIF(1)$_{348}$.

Recombinant molecule pVL1393-nDiMIF(1)$_{348}$ plasmid DNA was co-transfected into S. frugiperda Sf9 cells (donated by the Colorado Bioprocessing Center, Fort Collins, Co.) with wild type baculovirus DNA (AcMNPV) and insectin cationic liposomes (available from Invitrogen) to form recombinant cell S. frugiperda:pVL1393-nDiMIF (1)$_{348}$. The resulting recombinant virus, denoted Bv-nDiMIF(1)$_{348}$, was cultivated for increased production of recombinant virus and to verify expression of PDiMIF (1)$_{115}$. Immunoblot analysis using immune dog 2094–339 antisera demonstrated that total lysates of insect cells transfected with recombinant baculovirus Bv-nDiMIF(1)$_{348}$ expressed a protein, encoded by nDiMIF(1)$_{348}$, namely BvPDiMIF(1)$_{115}$, that migrated with an apparent molecular weight of about 19 kD.

Example 5

This Example describes the production of a MIF protein of the present invention in a eukaryotic cell.

Recombinant molecule pKB3poly-nMIF(1)$_{348}$, containing a D. immitis MIF nucleic acid molecule spanning nucleotides from about 8 through about 355 of SEQ ID NO:16 operatively linked to the vaccinia virus P$_{11}$ late promoter transcription control sequences was produced in the following manner. The pKB3poly poxvirus shuttle vector was created by modifying a region of plasmid pKB3 (P$_{11}$-type), pKB3 (P$_{11}$-type) plasmid is described in U.S. Pat. No. 5,348,741, by Esposito et al., issued Sep. 20, 1994)) such that the initiation codon linked to the P$_{11}$ promoter was mutated and additional unique polylinker restriction sites were added. The resulting poxvirus vector, referred to as pKB3poly, requires the insert DNA to provide the ATG initiation codon when inserted downstream of the P$_{11}$ promoter. The pKB3poly vector is designed such that foreign DNA cloned into the polylinker region of pKB3poly vector will recombine into the tk gene of wildtype poxvirus.

In order to subclone a MIF nucleic acid molecule into pKB3poly expression vector, MIF nucleic acid molecule-containing fragments were restricted from D. immitis pVL1393-nMIF(1)$_{348}$ DNA (produced as in Example 4), by BamHI and EcoRI restriction endonucleases. The about 348 nucleotide insert DNA (referred to as Rcn-nDiMIF(1)$_{348}$) was treated with Klenow enzyme to create blunt ends resulting in the production of nucleic acid molecule nRcnDiMIF(1)$_{348}$, gel purified and subcloned into the pKB3poly shuttle vector which had been restricted with SmaI restriction endonuclease, treated with calf intestinal phosphatase and gel purified to produce recombinant molecule pKB3poly-nDiMIF(1)$_{348}$. The proper orientation of the insert was verified by restriction mapping.

In order to produce a recombinant raccoon poxvirus capable of directing the production of PDiMIF(1)$_{115}$, BS-C-1 African green monkey kidney cells (obtained from American Type Culture Collection (ATCC), Rockville, Md.) were infected with wild type raccoon poxvirus RCN CDC/V71-I-85A) (obtained from Joe Esposito; Esposito and Knight 1985, Virology 143:230–251) and then transfected with the pKB3poly-nDiMIF(1)$_{348}$ vector DNA and lipofectAMINE (available from Gibco, BRL, Bethesda, Md.) to form recombinant cell BS-C-1:pKB3poly-nDiMIF(1)$_{348}$. The resulting recombinant virus, denoted Rcn-nDiMIF(1) $_{348}$, was cultivated in RAT2 rat embryo, thymidine kinase mutant cells (available from ATCC) in the presence of bromodeoxyuridine to select for TK⁻ recombinants.

Example 6

This Example describes the isolation and sequencing of two O. volvulus MIF nucleic acid molecules of the present invention. The O. volvulus MIF nucleic acid molecules were identified using a D. immitis MIF nucleic acid molecule of the present invention.

O. volvulus nucleic acid molecules nOvMIF(1)$_{440}$ and nOvMIF(2)$_{522}$ were produced in the following manner. An adult O. volvulus cDNA library (Touboro, Cameroun, available from ATCC) was screened with D. immitis MIF nucleic acid molecule nDiMIF(1)$_{355}$ using stringent hybridization conditions, which are known to those skilled in the art (see, for example, Sambrook et al., ibid.; such conditions typically permit isolation of nucleic acid molecules having at least about 70% nucleic acid sequence identity with the nucleic acid probe used in the hybridization). Several clones that hybridized with nDiMIF(1)$_{355}$, two of which were purified and submitted to nucleic acid sequence analysis. The nucleic acid sequence of an isolate containing an O. volvulus MIF nucleic acid molecule of about 440 nucleotides, denoted herein as nOvMIF(1)$_{440}$, is represented herein as SEQ ID NO:4. The nucleic acid sequence of the other isolate, which contained an O. volvulus MIF nucleic acid molecule of about 522 nucleotides, denoted herein as nOvMIF(2)$_{522}$, is represented herein as SEQ ID NO:7.

Translation of SEQ ID NO:4 yields an apparent full-length protein of about 115 amino acids, denoted POvMIF (1)$_{115}$, assuming a start codon spanning from about nucleotide 8 through about nucleotide 10, and a stop codon spanning from about nucleotide 353 through about nucleotide 355 of SEQ ID NO:4. The amino acid sequence of POvMIF(1)$_{115}$ is represented herein as SEQ ID NO:5. The coding region of POvMIF(1)$_{115}$ is referred to herein as nOvMIF(1)$_{345}$, the nucleic acid sequence of which is represented in SEQ ID NO:6. The amino acid sequence of *D. immitis* POvMIF(1)$_{115}$ (i.e., SEQ ID NO:5) predicts that POvMIF(1)$_{115}$ has an estimated molecular weight of about 12.24 kD and an estimated pI of about 9.21. There are 3 predicted N-glycosylation sites in the POvMIF(1)$_{115}$ deduced amino acid sequence, which are located in regions spanning amino acids from about 14 through about 16, from about 73 through about 75 and from about 110 through about 112 of SEQ ID NO:5.

Translation of SEQ ID NO:7 yields a protein of about 114 amino acids, denoted POvMIF(2)$_{114}$, assuming a stop codon spanning from about nucleotide 343 through about nucleotide 345 of SEQ ID NO:7. The amino acid sequence of POvMIF(2)$_{114}$ is represented herein as SEQ ID NO:8. The open reading frame encoding POvMIF(2)$_{115}$ is referred to herein as nOvMIF(2)$_{342}$, the nucleic acid sequence of which is represented in SEQ ID NO:9.

The two allelic variants SEQ ID NO:4 and SEQ ID NO:7 are identical in their coding regions (i.e., SEQ ID NO:6 and SEQ ID NO:9, respectively), except that (a) SEQ ID NO:7 apparently lacks a start codon; (b) SEQ ID NO:7 is about 10 nucleotides shorter than SEQ ID NO:4 at the 5' end; and (c) the region spanning from about nucleotide 1 through about nucleotide 19 of SEQ ID NO:7 is only about 47% identical to the region spanning from about nucleotide 10 through about nucleotide 29 of SEQ ID NO:4.

Comparison of nucleic acid molecules containing *O. volvulus* and *D. immitis* MIF coding regions (e.g., nOvMIF(1)$_{345}$ and nDiMIF(1)$_{345}$) indicated that the two MIF coding regions were about 87% identical at the nucleic acid sequence level. Comparison of apparent full-length *O. volvulus* and *D. immitis* MIF proteins (i.e., POvMIF(1)$_{115}$ and PDiMIF(1)$_{115}$) indicated that the two MIF proteins were about 88% identical at the amino acid level.

A homology search of the non-redundant protein sequence database, performed as described in Example 1 but using SEQ ID NO:5, showed significant homology to macrophage migration inhibition factor proteins of mammalian and avian origins, spanning from about amino acid 1 through about amino acid 115 of SEQ ID NO:5. The highest scoring match, i.e., 44% identity, was found between SEQ ID NO:5 and human and bovine MIFs. SEQ ID NO:5 was about 43% identical to rat, mouse and chicken MIFs. At the nucleotide level, the coding region represented in SEQ ID NO:6 was most similar to that of chicken migration inhibitory factor, being about 51% identical.

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
       (A) LENGTH: 532 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 8..355

(xi) SEQUENCE DESCRIPTION: SEQ ID NO: 1:

```
AAAAAAA ATG CCA TAT TTC ACG ATC GAT ACA AAC ATA CCA CAG GAC CGT        49
        Met Pro Tyr Phe Thr Ile Asp Thr Asn Ile Pro Gln Asp Arg
         1               5                  10

GTT TCG GAT GCA TTT CTA AAG AAG GCT TCA AGT ACG GTT GCA AAA GCA        97
Val Ser Asp Ala Phe Leu Lys Lys Ala Ser Ser Thr Val Ala Lys Ala
 15              20                  25                  30

CTT GGA AAA CCG GAA AGT TAC GTA TCA ATC CAT GTG AAT GGT GGA CAA       145
Leu Gly Lys Pro Glu Ser Tyr Val Ser Ile His Val Asn Gly Gly Gln
                 35                  40                  45

GCG ATG ACA TTC GGT GGA AGT ACA GAT CCA TGT GCT GTG TGT GTT TTA       193
Ala Met Thr Phe Gly Gly Ser Thr Asp Pro Cys Ala Val Cys Val Leu
             50                  55                  60

AAA TCA ATC GGT TCT GTT GGT CCC AGT GTG AAT AAT TCA CAC TGT GAG       241
Lys Ser Ile Gly Ser Val Gly Pro Ser Val Asn Asn Ser His Cys Glu
 65                  70                  75
```

-continued

```
AAA TTG TAC AAA TTG CTC GCT GAT GAG CTG AAA ATT CCG AAG AAT CGA      289
Lys Leu Tyr Lys Leu Leu Ala Asp Glu Leu Lys Ile Pro Lys Asn Arg
     80                  85                  90

TGC TAC ATC GAA TTT GTG GAT ATT AAT GCT TCT GCA ATG GGT TTT AAT      337
Cys Tyr Ile Glu Phe Val Asp Ile Asn Ala Ser Ala Met Gly Phe Asn
 95                 100                 105                 110

GGA TCT ACT TTC GGA TAATTGGTTT TTTACGGAAG AAATTGCAAT TTTTGGAAAT      392
Gly Ser Thr Phe Gly
            115

TATGAAACTT CAGTTGAAAA TTCCAGTTGT CGTTCTTTTT AATAAGATTT TCGTTTCCCA    452

TACTTTTTCT CTGTTACCTG GAATTTAAG TAATTATATG TTTGATAATA AAACTGTTTA     512

ATCAAAAAAA AAAAAAAAA                                                 532
```

(2) INFORMATION FOR SEQ ID NO: 2:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Pro Tyr Phe Thr Ile Asp Thr Asn Ile Pro Gln Asp Arg Val Ser
 1               5                  10                  15

Asp Ala Phe Leu Lys Lys Ala Ser Ser Thr Val Ala Lys Ala Leu Gly
             20                  25                  30

Lys Pro Glu Ser Tyr Val Ser Ile His Val Asn Gly Gly Gln Ala Met
         35                  40                  45

Thr Phe Gly Gly Ser Thr Asp Pro Cys Ala Val Cys Val Leu Lys Ser
     50                  55                  60

Ile Gly Ser Val Gly Pro Ser Val Asn Asn Ser His Cys Glu Lys Leu
 65                  70                  75                  80

Tyr Lys Leu Leu Ala Asp Glu Leu Lys Ile Pro Lys Asn Arg Cys Tyr
                 85                  90                  95

Ile Glu Phe Val Asp Ile Asn Ala Ser Ala Met Gly Phe Asn Gly Ser
            100                 105                 110

Thr Phe Gly
        115
```

(2) INFORMATION FOR SEQ ID NO: 3:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
ATGCCATATT TCACGATCGA TACAAACATA CCACAGGACC GAGTTTCGGA TGCATTTCTA     60

AAGAAGGCTT CAAGTACGGT TGCAAAAGCA CTTGGAAAAC CGGAAAGTTA CGTATCAATC    120

CATGTGAATG GTGGACAAGC GATGACATTC GGTGGAAGTA CAGATCCATG TGCTGTGTGT    180

GTTTTAAAAT CAATCGGTTC TGTTGGTCCC AGTGTGAATA ATTCACACTG TGAGAAATTG    240

TACAAATTGC TCGCTGATGA GCTGAAAATT CCGAAGAATC GATGCTACAT CGAATTTGTG    300

GATATTAATG CTTCTGCAAT GGGTTTTAAT GGATCTACTT TCGGA                    345
```

(2) INFORMATION FOR SEQ ID NO: 4:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 8..353

(xi) SEQUENCE DESCRIPTION: SEQ ID NO: 4:

```
GGGAGAA ATG CCT GCT TTT ACG ATC AAT ACA AAC ATA CCG CAG AGC AAT        49
        Met Pro Ala Phe Thr Ile Asn Thr Asn Ile Pro Gln Ser Asn
         1               5                  10

GTT TCG GAT GCG TTC CTA AAG AAG GCA TCA AGC ACG GTT GCG AAA CGA        97
Val Ser Asp Ala Phe Leu Lys Lys Ala Ser Ser Thr Val Ala Lys Arg
 15              20                  25                  30

CTT GGA AAG CCG GAA AGT TAT GTG GCA ATT CAT GTG AAT GGT GGA CAA       145
Leu Gly Lys Pro Glu Ser Tyr Val Ala Ile His Val Asn Gly Gly Gln
                 35                  40                  45

GCG ATG GTA TTC GGT GGA AGT ACT GAT CCA TGT GCT GTG TGT GTT TTA       193
Ala Met Val Phe Gly Gly Ser Thr Asp Pro Cys Ala Val Cys Val Leu
             50                  55                  60

AAA TCA ATC GGT TGT GTT GGT CCT AAT GTC AAT AAT TCG CAC TCT GAA       241
Lys Ser Ile Gly Cys Val Gly Pro Asn Val Asn Asn Ser His Ser Glu
 65                  70                  75

AAA TTG TTC AAA TTA CTC GCT GAT GAA TTG AAA ATT CCA AAA AAT CGA       289
Lys Leu Phe Lys Leu Leu Ala Asp Glu Leu Lys Ile Pro Lys Asn Arg
         80                  85                  90

TGC TAC ATC GAA TTT GTG AAT ATC GAT GCG TCT ACA ATG GCT TTT AAT       337
Cys Tyr Ile Glu Phe Val Asn Ile Asp Ala Ser Thr Met Ala Phe Asn
 95                 100                 105                 110

GGA TCT ACT TTT GGA T AATTGAATTT CGCAAAGGGA AATGTCATTT TCAGAAATT      393
Gly Ser Thr Phe Gly
                115

TGGAACTTTA GCTGAAATTT CTAGTTATTG TTCTTTTAAT TAATAAC                   440
```

(2) INFORMATION FOR SEQ ID NO: 5:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Pro Ala Phe Thr Ile Asn Thr Asn Ile Pro Gln Ser Asn Val Ser
 1               5                  10                  15

Asp Ala Phe Leu Lys Lys Ala Ser Ser Thr Val Ala Lys Arg Leu Gly
                 20                  25                  30

Lys Pro Glu Ser Tyr Val Ala Ile His Val Asn Gly Gly Gln Ala Met
             35                  40                  45

Val Phe Gly Gly Ser Thr Asp Pro Cys Ala Val Cys Val Leu Lys Ser
         50                  55                  60

Ile Gly Cys Val Gly Pro Asn Val Asn Asn Ser His Ser Glu Lys Leu
 65                  70                  75                  80

Phe Lys Leu Leu Ala Asp Glu Leu Lys Ile Pro Lys Asn Arg Cys Tyr
                 85                  90                  95
```

```
Ile Glu Phe Val Asn Ile Asp Ala Ser Thr Met Ala Phe Asn Gly Ser
            100                 105                 110
Thr Phe Gly
        115

(2) INFORMATION FOR SEQ ID NO: 6:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

ATGCCTGCTT TTACGATCAA TACAAACATA CCGCAGAGCA ATGTTTCGGA TGCGTTCCTA      60

AAGAAGGCAT CAAGCACGGT TGCGAAACGA CTTGGAAAGC CGGAAAGTTA TGTGGCAATT     120

CATGTGAATG GTGGACAAGC GATGGTATTC GGTGGAAGTA CTGATCCATG TGCTGTGTGT     180

GTTTTAAAAT CAATCGGTTG TGTTGGTCCT AATGTCAATA ATTCGCACTC TGAAAAATTG     240

TTCAAATTAC TCGCTGATGA ATTGAAAATT CCAAAAAATC GATGCTACAT CGAATTTGTG     300

AATATCGATG CGTCTACAAT GGCTTTTAAT GGATCTACTT TTGGA                    345

(2) INFORMATION FOR SEQ ID NO: 7:

(i) SEQUENCE CHARACTERISTICS:
        (A) LENGTH: 522 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..343

(xi) SEQUENCE DESCRIPTION: SEQ ID NO: 7:

AAA CCT TTT CCA CTC AGC TCA AAC ATA CCG CAG AGC AAT GTT TCG GAT        48
Lys Pro Phe Pro Leu Ser Ser Asn Ile Pro Gln Ser Asn Val Ser Asp
 1               5                  10                  15

GCG TTC CTA AAG AAG GCA TCA AGC ACG GTT GCG AAA CGA CTT GGA AAG        96
Ala Phe Leu Lys Lys Ala Ser Ser Thr Val Ala Lys Arg Leu Gly Lys
                20                  25                  30

CCG GAA AGT TAT GTG GCA ATT CAT GTG AAT GGT GGA CAA GCG ATG GTA       144
Pro Glu Ser Tyr Val Ala Ile His Val Asn Gly Gly Gln Ala Met Val
            35                  40                  45

TTC GGT GGA AGT ACT GAT CCA TGT GCT GTG TGT GTT TTA AAA TCA ATC       192
Phe Gly Gly Ser Thr Asp Pro Cys Ala Val Cys Val Leu Lys Ser Ile
 50                  55                  60

GGT TGT GTT GGT CCT AAT GTC AAT AAT TCG CAC TCT GAA AAA TTG TTC       240
Gly Cys Val Gly Pro Asn Val Asn Asn Ser His Ser Glu Lys Leu Phe
 65                  70                  75                  80

AAA TTA CTC GCT GAT GAA TTG AAA ATT CCA AAA AAT CGA TGC TAC ATC       288
Lys Leu Leu Ala Asp Glu Leu Lys Ile Pro Lys Asn Arg Cys Tyr Ile
                85                  90                  95

GAA TTT GTG AAT ATC GAT GCG TCT ACA ATG GCT TTT AAT GGA TCT ACT       336
Glu Phe Val Asn Ile Asp Ala Ser Thr Met Ala Phe Asn Gly Ser Thr
            100                 105                 110

TTT GGA T AATTGAATTT CGCAAAGGGA AATGTCATTT TCAGAAATTG TGGAACTTTA      393
Phe Gly
```

```
GCTGAAATTT CTAGTTATTG TTCTTTTAAT TAATAACATT TTTATTATCC ATACATTTTT      453

AAATTGTTAC TTGAAACTTT TAAGTGAAAT AGTGATTTGT TTGGTAATAA AACTATTTAA      513

TCAAAAAAA                                                              522
```

(2) INFORMATION FOR SEQ ID NO: 8:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO: 8:

```
Lys Pro Phe Pro Leu Ser Ser Asn Ile Pro Gln Ser Asn Val Ser Asp
  1               5                  10                  15

Ala Phe Leu Lys Lys Ala Ser Ser Thr Val Ala Lys Arg Leu Gly Lys
             20                  25                  30

Pro Glu Ser Tyr Val Ala Ile His Val Asn Gly Gly Gln Ala Met Val
         35                  40                  45

Phe Gly Gly Ser Thr Asp Pro Cys Ala Val Cys Val Leu Lys Ser Ile
     50                  55                  60

Gly Cys Val Gly Pro Asn Val Asn Asn Ser His Ser Glu Lys Leu Phe
 65                  70                  75                  80

Lys Leu Leu Ala Asp Glu Leu Lys Ile Pro Lys Asn Arg Cys Tyr Ile
                 85                  90                  95

Glu Phe Val Asn Ile Asp Ala Ser Thr Met Ala Phe Asn Gly Ser Thr
            100                 105                 110

Phe Gly
```

(2) INFORMATION FOR SEQ ID NO: 9:

(i) SEQUENCE CHARACTERISTICS:
        (A) LENGTH: 342 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

```
AAACCTTTTC CACTCAGCTC AAACATACCG CAGAGCAATG TTTCGGATGC GTTCCTAAAG       60

AAGGCATCAA GCACGGTTGC GAAACGACTT GGAAAGCCGG AAAGTTATGT GGCAATTCAT      120

GTGAATGGTG GACAAGCGAT GGTATTCGGT GGAAGTACTG ATCCATGTGC TGTGTGTGTT      180

TTAAAATCAA TCGGTTGTGT TGGTCCTAAT GTCAATAATT CGCACTCTGA AAAATTGTTC      240

AAATTACTCG CTGATGAATT GAAAATTCCA AAAAATCGAT GCTACATCGA ATTTGTGAAT      300

ATCGATGCGT CTACAATGGC TTTTAATGGA TCTACTTTTG GA                        342
```

(2) INFORMATION FOR SEQ ID NO: 10:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA

```
     (ix) FEATURE:
          (A) NAME/KEY: CDS
          (B) LOCATION: 1..103

(xi) SEQUENCE DESCRIPTION: SEQ ID NO: 10:

AAA TTG CTC GCT GAT GAG CTG AAA ATT CCG AAG AAT CGA TGC TAC ATC        48
Lys Leu Leu Ala Asp Glu Leu Lys Ile Pro Lys Asn Arg Cys Tyr Ile
 1               5                  10                  15

GAA TTT GTG GAT ATT AAT GCT TCT GCA ATG GGT TTT AAT GGA TCT ACT        96
Glu Phe Val Asp Ile Asn Ala Ser Ala Met Gly Phe Asn Gly Ser Thr
                20                  25                  30

TTC GGA T AATTGGTTTT TTACGGAAGA AATTGCAATT TTTGGAAATT ATGAAACTTC       153
Phe Gly

AGTTGAAAAT TCCAGTTGTC GTTCTTTTTA ATAAGATTTT CGTTTCCCAT ACTTTTTCTC      213

TGTTACCTGG GAATTTAAGT AATTATATGT TTGATAATAA AACTGTTTAA TCAAAAAAAA      273

AAAAAAAA                                                               282

(2) INFORMATION FOR SEQ ID NO: 11:

(i) SEQUENCE CHARACTERISTICS:
          (A) LENGTH: 34 amino acids
          (B) TYPE: amino acid
          (D) TOPOLOGY: linear (ii) MOLECULE TYPE: protein (xi) SEQUENCE DESCRIPTION: SEQ ID NO: 11:

Lys Leu Leu Ala Asp Glu Leu Lys Ile Pro Lys Asn Arg Cys Tyr Ile
 1               5                  10                  15

Glu Phe Val Asp Ile Asn Ala Ser Ala Met Gly Phe Asn Gly Ser Thr
                20                  25                  30

Phe Gly (2) INFORMATION FOR SEQ ID NO: 12:

(i) SEQUENCE CHARACTERISTICS:
          (A) LENGTH: 102 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 12:

AAATTGCTCG CTGATGAGCT GAAAATTCCG AAGAATCGAT GCTACATCGA ATTTGTGGAT       60

ATTAATGCTT GCAATGGG TTTTAATGGA TCTACTTTCG GA                           102

(2) INFORMATION FOR SEQ ID NO: 13:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (primer)

(xi) SEQUENCE DESCRIPTION: SEQ ID NO: 13:

CGCTCTAGAA CTAGTGGATC                                                   20
```

(2) INFORMATION FOR SEQ ID NO: 14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 14:

```
CCAATTATCC GAAAGTAGAT CC                                              22
```

(2) INFORMATION FOR SEQ ID NO: 15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 15:

```
CTTCGGAATT TTCAGCTCAT CAGCGAGC                                        28
```

(2) INFORMATION FOR SEQ ID NO: 16:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

```
AAAAAAAATG CCATATTTCA CGATCGATAC AAACATACCA CAGGACCGAG TTTCGGATGC      60
ATTTCTAAAG AAGGCTTCAA GTACGGTTGC AAAAGCACTT GGAAAACCGG AAAGTTACGT     120
ATCAATCCAT GTGAATGGTG ACAAGCGAT GACATTCGGT GGAAGTACAG ATCCATGTGC      180
TGTGTGTGTT TTAAAATCAA TCGGTTCTGT TGGTCCCAGT GTGAATAATT CACACTGTGA     240
GAAATTGTAC AAATTGCTCG CTGATGAGCT GAAAATTCCG AAGAATCGAT GCTACATCGA     300
ATTTGTGGAT ATTAATGCTT CTGCAATGGG TTTTAATGGA TCTACTTTCG GATAA          355
```

(2) INFORMATION FOR SEQ ID NO: 17:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

```
ATGCCATATT TCACGATCGA TACAAACATA CCACAGGACC GAGTTTCGGA TGCATTTCTA      60
AGAAGGCTT CAAGTACGGT TGCAAAAGCA CTTGGAAAAC CGGAAAGTTA CGTATCAATC      120
CATGTGAATG GTGGACAAGC GATGACATTC GGTGGAAGTA CAGATCCATG TGCTGTGTGT     180
GTTTTAAAAT CAATCGGTTC TGTTGGTCCC AGTGTGAATA ATTCACACTG TGAGAAATTG     240
TACAAATTGC TCGCTGATGA GCTGAAAATT CCGAAGAATC GATGCTACAT CGAATTTGTG     300
GATATTAATG CTTCTGCAAT GGGTTTTAAT GGATCTACTT TCGGA                    345
```

(2) INFORMATION FOR SEQ ID NO: 18:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

```
ATCGATACAA ACATACCACA GGACCGTGTT TCGGATGCAT TTCTAAAGAA GGCTTCAAGT      60

ACGGTTGCAA AAGCACTTGG AAAACCGGAA AGTTACGTAT CAATCCATGT GAATGGTGGA     120

CAAGCGATGA CATTCGGTGG AAGTACAGAT CCATGTGCTG TGTGTGTTTT AAAATCAATC     180

GGTTCTGTTG GTCCCAGTGT GAATAATTCA CACTGTGAGA AATTGTACAA ATTGCTCGCT     240

GATGAGCTGA AAATTCCGAA GAATCGATGC TACATCGAAT TTGTGGATAT TAATGCTTCT     300

GCAATGGGTT TTAATGGATC TACTTTCGGA TAA                                  333
```

(2) INFORMATION FOR SEQ ID NO: 19:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

```
ATCGATACAA ACATACCACA GGACCGTGTT TCGGATGCAT TTCTAAAGAA GGCTTCAAGT      60

ACGGTTGCAA AAGCACTTGG AAAACCGGAA AGTTACGTAT CAATCCATGT GAATGGTGGA     120

CAAGCGATGA CATTCGGTGG AAGTACAGAT CCATGTGCTG TGTGTGTTTT AAAATCAATC     180

GGTTCTGTTG GTCCCAGTGT GAATAATTCA CACTGTGAGA AATTGTACAA ATTGCTCGCT     240

GATGAGCTGA AAATTCCGAA GAATCGATGC TACATCGAAT TTGTGGATAT TAATGCTTCT     300

GCAATGGGTT TTAATGGATC TACTTTCGGA                                      330
```

(2) INFORMATION FOR SEQ ID NO: 20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 20:

```
GGACGGATCC AATGCCATAT TTCACGATC                                        29
```

(2) INFORMATION FOR SEQ ID NO: 21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 21:

```
GAGCGAATTC TTATCCGAAA GTAGATCC                                         28
```

-continued (2) INFORMATION FOR SEQ ID NO: 22:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 22:

CGCGGATCCT ATAAATATGC CATATTTCAC GATCG      35

(2) INFORMATION FOR SEQ ID NO: 23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 23:

CCGGAATTCT TATCCGAAAG TAGATCC      27

While various embodiments of the present invention have been described in detail, it is apparent that modifications and adaptations of those embodiments will occur to those skilled in the art. It is to be expressly understood, however that such modifications and adaptations are within the scope of the present invention, as set forth in the following claims.

What is claimed is:

1. An isolated antibody that selectively binds to a protein comprising an amino acid sequence selected from the group consisting of SEQ ID NO:2 and SEQ ID NO:11.

2. The antibody of claim 1, wherein said protein is encoded by a nucleic acid molecule comprising a nucleic acid sequence selected from the group consisting of SEQ ID NO:3, SEQ ID NO:12, SEQ ID NO:17, and SEQ ID NO:19.

3. The antibody of claim 1, wherein said antibody is a monoclonal antibody.

4. The antibody of claim 1, wherein said antibody is a polyclonal antibody.

5. A composition comprising an excipient and an isolated antibody that selectively binds to a protein comprising an amino acid sequence selected from the group consisting of SEQ ID NO:2 and SEQ ID NO:11.

6. The composition of claim 5, wherein said composition further comprises a component selected from the group consisting of an adjuvant and a carrier.

7. The composition of claim 5, wherein said protein is encoded by a nucleic acid molecule comprising a nucleic acid sequence selected from the group consisting of SEQ ID NO:3, SEQ ID NO:12, SEQ ID NO:17, and SEQ ID NO:19.

8. The composition of claim 5, wherein said antibody is a monoclonal antibody.

9. The composition of claim 5, wherein said antibody is a polyclonal antibody.

\* \* \* \* \*